(12) United States Patent
Matsumura et al.

(10) Patent No.: US 7,626,034 B2
(45) Date of Patent: Dec. 1, 2009

(54) ASYMMETRIC REDUCTIVE AMINATION OF KETO ACID DERIVATIVES FOR PRODUCING AMINO ACID DERIVATIVES

(75) Inventors: Kazuhiko Matsumura, Hiratsuka (JP); Takao Saito, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 26 days.

(21) Appl. No.: 10/571,855

(22) PCT Filed: Sep. 17, 2004

(86) PCT No.: PCT/JP2004/014048
§ 371 (c)(1),
(2), (4) Date: Apr. 26, 2006

(87) PCT Pub. No.: WO2005/028419
PCT Pub. Date: Mar. 31, 2005

(65) Prior Publication Data
US 2007/0142443 A1 Jun. 21, 2007

(30) Foreign Application Priority Data
Sep. 18, 2003 (JP) ............................. 2003-326939

(51) Int. Cl.
C07D 211/70 (2006.01)
(52) U.S. Cl. ..................... 546/335; 548/561; 560/115
(58) Field of Classification Search ................ 564/335; 548/561; 560/155; 546/335
See application file for complete search history.

(56) References Cited

U.S. PATENT DOCUMENTS

| | | | |
|---|---|---|---|
| 3,644,356 A | 2/1972 | Chakrabarti et al. | |
| 4,521,624 A | 6/1985 | Jackisch | |
| 4,585,887 A * | 4/1986 | Jolidon et al. ................ | 560/38 |
| 6,646,130 B2 * | 11/2003 | Rivera et al. ................ | 546/301 |
| 6,884,887 B1 | 4/2005 | Riermeier et al. | |
| 6,949,677 B2 * | 9/2005 | Glufke et al. ................ | 564/200 |
| 7,145,030 B2 * | 12/2006 | Hamada et al. ............... | 560/43 |
| 7,468,459 B2 * | 12/2008 | Xiao et al. ................... | 564/336 |
| 2004/0147762 A1 | 7/2004 | Zhang | |

OTHER PUBLICATIONS

Kadyrov et al., The First Highly Enantioselective Homogeneously Catalyzed Asymmetric Reductive Amination: Synthesis of -N-Benzylamino Acids, J. Org. Chem., 2003; 68(10); 4067-4070.*
Tararov et al., On the reductive amination of aldehydes and ketones catalyzed by homogeneous Rh(I) complexes, Chem. Commun., 2000, 1867-1868.*
Marigo et al., Direct catalytic asymmetric Mannich reactions of malonates and -keto esters, Chemistry—A European Journal (2003), 9(10), 2359-2367.*
Marigo et al., Direct catalytic asymmetric Mannich reactions of malonates and □-keto esters, Chemistry—A European Journal (2003), 9(10), 2359-2367.*
Zhou et al., Highly Effective Chiral Ortho-Substituted BINAPO Ligands (o-BINAPO): Applications in Ru-Catalyzed, Asymmetric Hydrogenations of b-Aryl-Substituted b-(Acylamino)acrylates and b-Keto Esters, Journal of the American Chemical Society (2002), 124(18), 4952-4953.*
Mannich reaction, From Wikipedia, the free encyclopedia, page was last modified on Jun. 23, 2008.*
Cohen et al., Stereoselective synthesis of .beta.-aryl-.beta.-amino esters, Tetrahedron Letters (2002), 43(11), 1977-1981.*
R. Kadyrov et al., "The First Highly Enantioselective Homogeneously Catalyzed Asymmetric Reductive Amination: Synthesis of a-N-Benzylamino Acids", Journal of Organic Chemistry, vol: 68, No. 10, pp. 4067-4070, 2003.
V. Tararov et al., "On the reductive amination of aldehydes and ketones catalyzed by homogeneous Rh(I) complexes", Chemical Communications, pp. 1867-1868, 2000.
Gomez, S. et al., "The Reductive Amination of Aldehydes and Ketones and the Hydrogenation of Nitriles: Mechanistic Aspects and Selectivity Control," Adv. Synth, Catal., 344:10, 2002, 1037-1057.
Tararov, V.I., et al., "A Scrutiny on the Reductive Amination of Carbonyl Compounds Catalyzed by Homogeneous Rh(I) Diphosphane Complexes," Adv. Synth. Catal., 344:2, 2002, pp. 200-208.
Bunlaksananusorn, T. et al., "A Facile One-Pot Synthesis of Chiral beta-Amino Esters," Synlett, No. 17, 2005, pp. 2682-2684.
Renat Kadyrov et al.; the First Highly Enantioselective Homogeneously Catalzyed Asymmetric Reductive Amination: Synthesis of a-N--Benzylamino Acids; J Org. Chemical 2003, 68, 4067-4070.
Vitali I. Tararov et al.; On the reducutive amination of adkehydes and ketones catalyzed by homogeneous Rh(I) complexes; Chemical Comun., 2000, 1867-1868.

* cited by examiner

*Primary Examiner*—Jafar Parsa
*Assistant Examiner*—Chukwuma O Nwaonicha
(74) *Attorney, Agent, or Firm*—Sughrue Mion, PLLC

(57) ABSTRACT

The present invention relates to a process for producing amino acid derivatives such as optically active β-amino acid in short steps with good yield and high optical purity, which comprises reacting a keto acid of the formula (1):

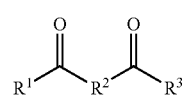

(1)

wherein $R^1$ is hydrogen, an optionally substituted hydrocarbon, etc.; $R^2$ is a spacer; and $R^3$ is an optionally substituted alkoxy, etc., or a salt thereof, with ammonia or an amine or a salt thereof in the presence of a chiral catalyst and in the presence or absence of an acid and/or a fluorine-containing alcohol, to give an amino acid derivative of the formula (2):

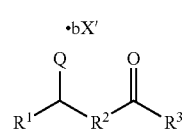

(2)

wherein Q is a group formed by removing one hydrogen atom from ammonia or an amine; X' is an acid and/or a fluorine-containing alcohol; and b is 0 or 1.

8 Claims, No Drawings

ASYMMETRIC REDUCTIVE AMINATION OF KETO ACID DERIVATIVES FOR PRODUCING AMINO ACID DERIVATIVES

This application is a U.S. national stage of International Application No. PCT/JP2004/014048 filed Sep. 17, 2004.

TECHNICAL FIELD

This invention relates to a process for producing an amino acid derivative useful as intermediates for medicines, agrochemicals, etc.

BACKGROUND ART

Hitherto, the following are known as methods for synthesizing optically active β-amino acid derivatives: (1) a method of synthesizing a racemate of desired amino acids, followed by optical resolution using an optically active resolving agent or an enzyme; (2) a method of the catalytic asymmetric hydrogenation of β-acylamino-α,β-unsaturated esters; or (3) a synthetic method via enamines prepared from β-ketoesters and optically active amines.

Among them, Patent Literature No. 1 discloses, as a method using a β-ketoester and an optically active amine, that a β-ketoester is reacted with an optically active phenethylamine to give an enamine, followed by reaction in the presence of a palladium catalyst and hydrogen, whereby optically active β-amino acid derivatives are synthesized. However, in the method disclosed in Patent Literature No. 1, the optically active phenethylamine which is an expensive reagent is required in an amount of more than stoichiometric amount to the β-ketoester, and the optically active phenethyl group which is a protective group has to be deprotected, rendering problems of high cost and poor operating efficiency.

In addition, Non-Patent Literature No. 1 discloses that after enamine formation by the reaction between β-ketoester and optically active phenethylamine, said enamine is reduced in the presence of sodium borohydride and an acid, yielding optically active β-amino acid derivatives. However, in the method disclosed in Non-Patent Literature No. 1, it requires an optically active amine which is an expensive reagent, in an amount of more than stoichiometric amount to the ketone, similarly as is in the method of Patent Literature No. 1, resulting in drawbacks such as high cost and poor operating efficiency due to the reaction via enamines used as intermediates.

Further, Non-Patent Literature No. 2 discloses a synthesis of optically active α-amino acid derivatives by reacting an α-keto acid with benzylamine in the presence of a catalyst and hydrogen. Non-Patent Literature No. 3 discloses a synthetic method for α-amino acid derivatives by reacting an α-keto acid with ammonium formate in the presence of a catalyst. Moreover, Non-Patent Literature No. 4 discloses a method for synthesizing N-benzyl-α-phenylalanine, which is an amino acid derivative, by reacting phenylpyruvic acid as α-keto acid with benzylamine in the presence of a catalyst and hydrogen. However, nothing is mentioned with respect to synthetic methods for optically active β-amino acid derivatives in these Non-Patent Literatures Nos. 2 to 4.

[Patent Literature No. 1] WO 00/56716
[Non-Patent Literature No. 1] (Tetrahedron:Asymmetry), 1997, vol. 8, p. 1445 to 1451.
[Non-Patent Literature No. 2] J. Org. Chem. 2003, vol. 68, p. 4067 to 4070.
[Non-Patent Literature No. 3] J. Org. Chem. 2002, vol. 67, p. 8685 to 8687.
[Non-Patent Literature No. 4] Chem. Commun. 2000, p. 1867 to 1868.

DISCLOSURE OF THE INVENTION

It is an object of the present invention to provide a process for producing an amino acid derivative such as β-amino acid derivatives, especially optically active β-amino acid derivatives through shorter steps from easily available starting materials in good yield with high optical purity.

The present inventors have studied intensively to solve the above-mentioned problems and have found that when a starting keto acid derivative such as β-keto acid derivative is reacted with ammonia or an amine or a salt thereof as a starting material in the presence of a chiral catalyst and hydrogen, amino acid derivatives such as desired optically active β-amino acid derivatives can be produced in shorter steps with good yield and high optical purity. The present invention has been accomplished on the basis of these findings.

Namely, the present invention relates to the following.

(1) A process for producing an amino acid derivative of the formula (2):

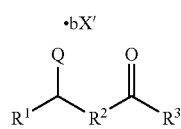

wherein
R$^1$ is a hydrogen atom, an optionally substituted hydrocarbon group or an optionally substituted heterocyclic group;

R$^2$ is a spacer;

R$^3$ is an optionally substituted alkoxy group, an optionally substituted aryloxy group, an optionally substituted aralkyloxy group, hydroxy, —NR$^a$R$^b$ (R$^a$ and R$^b$ are each independently a hydrogen atom, an optionally substituted hydrocarbon group, an optionally substituted acyl group, —SO$_2$A$^1$ (A$^1$ is an optionally substituted hydrocarbon group or a substituted amino group), —COOR$^c$ (R$^c$ is an optionally substituted hydrocarbon group) or an optionally substituted heterocyclic group; or R$^1$ and R$^2$, R$^2$ and R$^3$, or R$^1$ and R$^3$, taken together, may form a ring;

Q is a group formed by removing one hydrogen atom from ammonia or an amine;

X' is an acid and/or a fluorine-containing alcohol; and b is 0 or 1, or a salt thereof, which comprises reacting a keto acid of the formula (1):

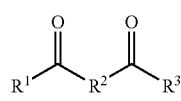

wherein R$^1$ to R$^3$ have each the same meaning as defined above, with ammonia or an amine or a salt thereof in the presence of a chiral catalyst and hydrogen gas and in the presence or absence of an acid and/or a fluorine-containing alcohol.

(2) The process according to the above (1), wherein the amino acid derivative of the formula (2) is an optically active amino acid derivative of the formula (2-1):

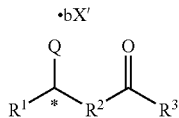

(2-1)

wherein
$R^1$ is a hydrogen atom, an optionally substituted hydrocarbon group or an optionally substituted heterocyclic group;
$R^2$ is a spacer;
$R^3$ is an optionally substituted alkoxy group, an optionally substituted aryloxy group, an optionally substituted aralkyloxy group, hydroxy, —$NR^aR^b$ ($R^a$ and $R^b$ are each independently a hydrogen atom, an optionally substituted hydrocarbon group, an optionally substituted acyl group, —$SO_2A^1$ ($A^1$ is an optionally substituted hydrocarbon group or a substituted amino group), —$COOR^c$ ($R^c$ is an optionally substituted hydrocarbon group) or an optionally substituted heterocyclic group;
X' is an acid and/or a fluorine-containing alcohol;
b is 0 or 1; or
$R^1$ and $R^2$, $R^2$ and $R^3$, or $R^1$ and $R^3$, taken together, may form a ring;
Q is a group formed by removing one hydrogen atom from ammonia or an amine; and
* is a chiral carbon atom.

(3) The process according to the above (1), wherein the ammonia, amine or a salt thereof is an amine or a salt thereof, represented by the formula (3):

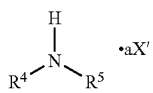

(3)

wherein
$R^4$ and $R^5$ are each independently a hydrogen atom, an optionally substituted hydrocarbon group, an optionally substituted heterocyclic group, an optionally substituted alkoxy group, an optionally substituted aryloxy group or an optionally substituted aralkyloxy group; or
$R^4$ and $R^5$ taken together may form a ring;
X' is an acid and/or a fluorine-containing alcohol; and
a is 0 or 1.

(4) The process according to the above (1), wherein the amino acid derivative or salt thereof is an amino acid derivative or salt thereof, represented by the formula (2a):

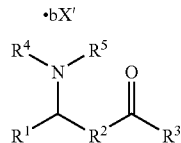

(2a)

wherein
$R^1$ is a hydrogen atom, an optionally substituted hydrocarbon group or an optionally substituted heterocyclic group;
$R^2$ is a spacer;
$R^3$ is an optionally substituted alkoxy group, an optionally substituted aryloxy group, an optionally substituted aralkyloxy group, hydroxy, —$NR^aR^b$ ($R^a$ and $R^b$ are each independently a hydrogen atom, an optionally substituted hydrocarbon group, an optionally substituted acyl group, —$SO_2A^1$ ($A^1$ is an optionally substituted hydrocarbon group or a substituted amino group), —$COOR^c$ ($R^c$ is an optionally substituted hydrocarbon group) or an optionally substituted heterocyclic group;
$R^4$ and $R^5$ are each independently a hydrogen atom, an optionally substituted hydrocarbon group, an optionally substituted heterocyclic group, an optionally substituted alkoxy group, an optionally substituted aryloxy group or an optionally substituted aralkyloxy group;
X' is an acid and/or a fluorine-containing alcohol;
b is 0 or 1; or
$R^1$ and $R^2$; $R^2$ and $R^3$; $R^1$ and $R^3$; or $R^4$ and $R^5$, taken together, may form a ring.

(5) A process for producing an optically active β-amino acid derivative of the formula (2-2):

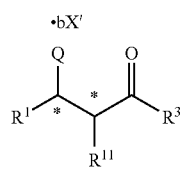

(2-2)

wherein
$R^1$ is a hydrogen atom, an optionally substituted hydrocarbon group or an optionally substituted heterocyclic group;
$R^3$ is an optionally substituted alkoxy group, an optionally substituted aryloxy group, an optionally substituted aralkyloxy group, hydroxy, —$NR^aR^b$ ($R^a$ and $R^b$ are each independently a hydrogen atom, an optionally substituted hydrocarbon group, an optionally substituted acyl group, —$SO_2A^1$ ($A^1$ is an optionally substituted hydrocarbon group or a substituted amino group), —$COOR^c$ ($R^c$ is an optionally substituted hydrocarbon group) or an optionally substituted heterocyclic group;
$R^{11}$ is a hydrogen atom, an optionally substituted hydrocarbon group, an optionally substituted alkoxy group, an optionally substituted aryloxy group, an optionally substituted aralkyloxy group or hydroxy;
$R^1$ and $R^{11}$; $R^{11}$ and $R^3$; or $R^3$ and $R^1$, taken together, may form a ring;
Q is a group formed by removing one hydrogen atom from ammonia or an amine;

X' is an acid and/or a fluorine-containing alcohol;
b is 0 or 1; and
* is a chiral carbon atom, or a salt thereof, which comprises reacting a β-keto acid derivative of the formula (1-1):

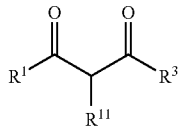
(1-1)

wherein $R^1$, $R^{11}$ and $R^3$ have each the same meaning as defined above, with ammonia or an amine or a salt thereof in the presence of a chiral catalyst and hydrogen, and in the presence or absence of an acid and/or a fluorine-containing alcohol.

(6) The process according to the above (1) or (5), wherein the chiral catalyst is a transition metal complex.

(7) The process according to the above (6), wherein the transition metal complex is a complex of metal of Groups 8 to 10.

(8) The process according to the above (6), wherein the transition metal complex has a chiral ligand.

(9) The process according to the above (6), wherein the chiral ligand is a chiral phosphine ligand.

(10) The process according to the above (1) or (5), wherein the chiral catalyst is a chiral transition metal complex of the formula (7) or (8):

(7)

(8)

wherein M is a transition metal of Groups 8 to 10; L is a chiral ligand; X is a halogen atom, a carboxylato group, allyl, 1,5-cyclooctadiene or norbornadiene; Y is a ligand; Z is an anion or a cation; m, n, p, q and s are each an integer of 0 to 5.

(11) The process according to the above (1) or (5), wherein the chiral catalyst is a mixture of a chiral ligand and a transition metal compound.

The present process has excellent advantages in that amino acid derivatives such as β-amino acid derivatives can be produced effectively from easily available starting materials (keto acids and ammonia or amines or salts thereof) in shorter steps, and desired optically active β-amino acid derivatives can be produced in a good yield with high optical purity. Furthermore, the process of the present invention exhibits a remarkable effect in that not only optically active amino acid derivatives having an unsubstituted amino group can be produced directly without deprotection step, but also desired optically active amino acid derivatives can be produced even by use of amines having a substituent such as aryl and alkyl which have a desired halogenated hydrocarbon group, etc.

THE BEST MODE FOR CARRYING OUT THE INVENTION

One of the starting materials used in the present invention is a keto acid derivative of the formula:

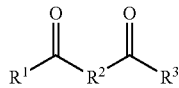
(1)

wherein $R^1$ to $R^3$ have each the same meaning as defined above.

Each group in the above formula will be illustrated below.

The optionally substituted hydrocarbon group represented by $R^1$ includes an unsubstituted hydrocarbon group and a substituted hydrocarbon group. Examples of the hydrocarbon group include, for example, alkyl, alkenyl, alkynyl, aryl and aralkyl.

The alkyl group may be linear, branched, or cyclic, such as an alkyl group of 1 to 15 carbon atoms, preferably 1 to 10 carbon atoms. Specific examples of such alkyl groups are methyl, ethyl, n-propyl, 2-propyl, n-butyl, 2-butyl, isobutyl, tert-butyl, n-pentyl, 2-pentyl, tert-pentyl, 2-methylbutyl, 3-methylbutyl, 2,2-dimethylpropyl, n-hexyl, 2-hexyl, 3-hexyl, tert-hexyl, 2-methylpenyl, 3-methylpentyl, 4-methylpentyl, 2-methylpentan-3-yl, heptyl, octyl, nonyl, decyl, cyclopropyl, cyclobutyl, cyclopentyl, cyclohexyl, etc.

The alkenyl group may be straight or branched, and includes an alkenyl group with carbon atoms of, for example, 2 to 15, preferably 2 to 10, more preferably 2 to 6, such as ethenyl, propenyl, 1-butenyl, pentenyl, hexenyl, etc.

The alkynyl group may be straight or branched, and includes an alkynyl group with carbon atoms of, for example, 2 to 15, preferably 2 to 10, more preferably 2 to 6, such as ethynyl, 1-propynyl, 2-propynyl, 1-butynyl, 3-butynyl, pentynyl, hexynyl, etc.

The aryl group includes, for example, an aryl group with carbon atoms of 6 to 14, and specific examples of such aryl group are phenyl, naphthyl, anthoryl, biphenyl, etc.

The aralkyl group includes, for example, a group wherein at least one hydrogen atom in said alkyl group is substituted by said aryl group, and such aralkyl group is preferably an aralkyl group with carbon atoms of 7 to 15, including benzyl, 2-plenylethyl, 1-phenylpropyl, 3-naphthylpropyl, etc.

The substituted hydrocarbon group (hydrocarbon group having a substituent) is a hydrocarbon group wherein at least one hydrogern atom of the aforementioned hydrocarbon group is substituted by a substituent which will be mentioned hereinafter.

The optionally substituted heterocyclic group includes an unsubstituted heterocyclic group and a substituted heterocyclic group, and examples of such heterocyclic groups are an aliphatic heterocyclic group and an aromatic heterocyclic group.

The aliphatic heterocyclic group is, for example, a 5- to 8-membered, or more preferably, 5- to 6-membered monocyclic, polycyclic or fused-ring aliphatic heterocyclic group which is composed of 2 to 14 carbon atoms, and contains as heteroatoms at least one heteroatom, more preferably 1 to 3 heteroatoms, such as nitrogen, oxygen, sulfuratoms, etc. Specific examples of such aliphatic heterocyclic group include, for example, 2-oxo-pyrrolidinyl, piperidino, piperazinyl, morpholino, tetrahydrofuryl, tetrahydropyranyl, etc.

The aromatic heterocyclic group is, for example, a 5- to 8-membered, more preferably, 5- to 6-membered monocyclic, polycyclic or fused-ring aromatic heterocyclic group which is composed of 2 to 15 carbon atoms, and as heteroatoms, at least one heteroatom, and more preferably 1 to 3 heteroatoms such as nitrogen, oxygen, sulfur atoms, etc. Specific examples of such aromatic heterocyclic group include, for example, furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzoxazolyl, benzothiazolyl, etc.

The substituted heterocyclic group (heterocyclic group having a substituent) includes a heterocyclic group wherein at least one hydrogen atom in said heterocylic groups is substituted by a substituent which will be described hereinafter.

The optionally substituted alkoxy group represented by $R^3$ includes an alkoxy group and a substituted alkoxy group. As the alkoxy group are exemplified straight, branched or cyclic alkoxy groups of, for example, 1 to 6 carbon atoms. Specific examples of such alkoxy group include, for example, methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, etc. As the substituted alkoxy group are mentioned those wherein at least one hydrogen atom in said alkoxy group is substituted by a substituent which will be described hereinafter.

The optionally substituted aryloxy group includes an aryloxy group and a substituted aryloxy group. As such aryloxy group are mentioned, for example, those of 6 to 14 carbon atoms. Specific examples of such aryloxy group include phenyloxy, naphthyloxy, anthryloxy, etc. The substituted aryloxy group can be those wherein at least one hydrogen atom in said aryloxy group is substituted by a substituent which will be described hereinafter.

The optionally substituted aralkyloxy group is an aralkyloxy group and a substituted aralkyloxy group. As such aralkyloxy group are mentioned those of, for example, 7 to 15 carbon atoms. Specific examples of such aralkyloxy group include benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, etc. The substituted aralkyloxy group can be those wherein at least one hydrogen atom in said aralkyloxy group is substituted by a substituent which will be described hereinafter.

The optionally substituted hydrocarbon group represented by $R^a$ and $R^b$ in $-NR^aR^b$ is the same as the aforementioned optionally substituted hydrocarbon group. When at least one of $R^a$ and $R^b$ is an optionally substituted hydrocarbon group, examples of $-NR^aR^b$ are methylamino, dimethylamino, diethylamino, dipropylamino, diusopropylamino, benzylamino, etc.

The optionally substituted acyl group includes an acyl group and a substituted acyl group, and said acyl group may be linear, branched or cyclic. For example, there are mentioned acyl groups of 1 to 18 carbon atoms derived from carboxylic acids such as aliphatic carboxylic acids and aromatic carboxylic acids. Specific examples of such acyl groups are formyl, acetyl, propionyl, butyryl, pivaloyl, pentanoyl, hexanoyl, lauroyl, stearoyl, benzoyl, etc.

When at least one of $R^a$ and $R^b$ is an optionally substituted acyl, examples of $-NR^aR^b$ are N-acetylamino, N-benzoylamino, etc.

The optionally substituted hydrocarbon groups represented by $A^1$ of $-SO_2A^1$ are the same as the aforementioned optionally substituted hydrocarbon group. The substituted amino group will be described below, and preferred substituted amino groups are those wherein two hydrogen atoms of the amino group are substituted by the aforementioned optionally substituted hydrocarbon group.

Examples of $-SO_2A^1$ are $-SO_2CH_3$, $-SO_2C_6H_5$, $-SO_2C_6H_4CH_3$, $-SO_2CF_3$, $-SO_2N(CH_3)_2$, etc. Specific examples of $-NR^aR^b$ in the case where at least one of $R^a$ and $R^b$ is $-SO_2A^1$ are $-NHSO_2CH_3$, $-NHSO_2C_6H_5$, $-NHSO_2C_6H_4CH_3$, $-NHSO_2CF_3$, $-NHSO_2N(CH_3)_2$, etc.

The optionally substituted hydrocarbon groups represented by $R^c$ of $-COOR^c$ are the same as those as mentioned above examples of $-COOR^c$ are methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, phenoxycarbonyl, naphthyloxycarbonyl, benzyloxycarbonyl, phenylethoxycarbonyl, 9-fluorenylmethoxycarbonyl, etc. Specific examples of $-NR^aR^b$, i.e. $-NHCOOR^c$ in the case where at least one of $R^a$ and $R^b$ is $-COOR^c$ are methyl carbamate, ethyl carbamate, etc.

The optionally substituted heterocyclic group represented by $R^3$ includes a cyclic group which contains at least one hetero atom such as nitrogen, oxygen and/or sulfur among ring-constituting atoms, and said heterocyclic ring may be a monocyclic, polycyclic, or fused ring containing optionally a substituent which will be described hereinafter, preferably a ring represented by the formula given below:

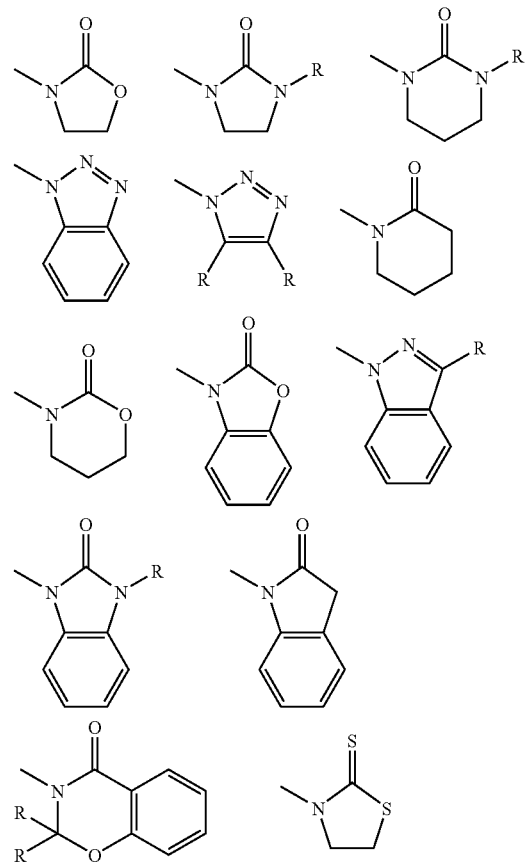

-continued

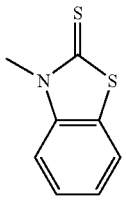

In the above formulae, R is the same or different hydrogen or a substituent which will be described hereinafter, and the above-mentioned heterocylic group may have, other than R, a substituent which will be described hereinafter.

As the substituents in various substituted groups such as substituted hydrocarbon groups, substituted heterocyclic groups, substituted acyl groups, substituted alkoxy groups, substituted aryloxy groups, substituted aralkyloxy groups, etc. are mentioned hydrocarbon groups, substituted hydrocarbon groups, heterocyclic groups, substituted heterocyclic groups, alkoxy groups, substituted alkoxy groups, aryloxy groups, substituted aryloxy groups, aralkyloxy groups, substituted aralkyloxy groups, acyl groups, substituted acyl groups, alkoxycarbonyl groups, aryloxycarbonyl groups, aralkyloxycarbonyl groups, acyloxy groups, alkylthio groups, aralkylthio groups, arylthio groups, halogen atoms, halogenated hydrocarbon groups, alkylenedioxy groups, amino groups, substituted amino groups, cyano group, nitro group, hydroxy group, carboxyl group, sulfo group, substituted silyl groups, etc.

The hydrocarbon groups, substituted hydrocarbon groups, heterocyclic groups and substituted heterocyclic groups are the same as each group of $R^1$ mentioned above. The alkoxy groups, substituted alkoxy groups, aryloxy groups, substituted aryloxy groups, aralkyloxy groups, substituted aralkyloxy groups, acyl groups and substituted acyl groups are each the same as each group of $R^3$ as mentioned above.

The alkoxycarbonyl group includes linear, branched, or cyclic alkoxycarbonyl groups of, for example, 2 to 19 carbon atoms. Specific examples of the alkoxycarbonyl group are methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl, etc.

The aryloxycarbonyl group includes, for example, aryloxycarbonyl groups of 7 to 20 carbon atoms, such as phenoxycarbonyl, naphthyloxycarbonyl, etc.

The aralkyloxycarbonyl group includes, for example, aralkyloxycarbonyl groups of 8 to 15 carbon atoms, and specific examples of such aralkyloxycarbonyl groups are benzyloxycarbonyl, phenylethoxycarbonyl, 9-fluorenylmethyloxy-carbonyl, etc.

The acyloxy group includes, for example, acyloxy groups of 2 to 18 carbon atoms, derived from carboxylic acids such as aliphatic carboxylic acids, aromatic carboxylic acids, etc. Specific examples of such acyloxy groups are acetoxy, propionyloxy, butyryloxy, pivaloyloxy, pentanoyloxy, hexanoyloxy, lauroyloxy, stearoyloxy, benzoyloxy, etc.

The alkylthio group may be linear, branched, or cyclic, and includes alkylthio groups of 1 to 6 carbon atoms. Specific examples of such alkylthio groups are methylthio, ethylthio, n-propylthio, 2-propylthio, n-butylthio, 2-butylthio, isobutylthio, tert-butylthio, pentylthio, hexylthio, cyclohexylthio, etc.

The arylthio group includes, for example, arylthio groups of 6 to 14 carbon atoms, such as phenylthio, naphthylthio, etc.

The aralkylthio group includes, for example, aralkylthio groups of 7 to 15 carbon atoms, and specific examples of such aralkylthio groups are benzylthio, 2-phenethylthio, etc.

The halogen atom includes fluorine, chlorine, bromine and iodine.

The halogenated hydrocarbon groups are those formed by halogenation (e.g. fluorination, chlorination, bromination, iodination) of at least one hydrogen atom of the above-mentioned hydrocarbon groups. Specific examples of such a halogenated hydrocarbon group are alkyl halides such as alkyl halide of 1 to 10 carbon atoms, including chloromethyl, bromomethyl, 2-chloroethyl, 3-bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, 2-perfluorooctylethyl, perfluorocyclopropyl, perfluorocyclopentyl, perfluorocyclohexyl, etc.

The alkylenedioxy groups as a substituent are those formed by substituting two adjacent hydrogen atoms in the aromatic ring of the above-mentioned aryl group or aralkyl group, by an alkylenedioxy group. Specific examples of such an alkylenedioxy group are methylenedixoy, ethylenedioxy, trimethylenedioxy, propylenedioxy, etc.

The substituted amino groups include an amino group wherein one or two hydrogen atoms of the amino group is/are substituted by a substituent such as a protecting group. Any protecting group can be used as far as it can be used as an amino-protecting group, and there are exemplified those which are described as an amino-protecting group in PROTECTIVE GROUPS IN ORGANIC SYNTHESIS THIRD EDITION (JOHN WILEY & SONS, INC. (1999)). Specific examples of such an amino-protecting group are alkyl, aryl, aralkyl, acyl, alkoxycarbonyl, aryloxycarbonyl, aralkyloxycarbonyl, etc.

The alkyl, aryl, and aralkyl groups of the above-mentioned amino-protecting group are the same with each group of the hydrocarbon groups of $R^1$ mentioned above, and the acyl groups are the same as those of $R^3$ mentioned above. The alkoxycarbonyl, aryloxycarbonyl, and aralkyloxycarbonyl groups are the same with each group of the above-mentioned substituents. The amino groups substituted with an alkyl group, i.e. alkyl-substituted amino groups include mono- and di-alkylamino groups such as N-methylamino, N,N-dimethylamino, N,N-diethylamino, N,N-diisopropylamino, N-cyclohexylamino, etc. The amino groups substituted by an aryl group, i.e. aryl-substituted amino groups include mono- and di-arylamino groups such as N-phenylamino, N,N-diphenylamino, N-naphthylamino, N-naphthyl-N-phenylamino, etc. The amino groups substituted with an aralkyl group, i.e. aralkyl-substituted amino groups include, for example, mono and di-aralkylamino groups such as N-benzylamino, N,N-dibenzylamino, etc. The amino groups substituted by an acyl group, i.e. an acylamino groups include, for example, formylamino, acetylamino, propionylamino, pivaloylamino, pentanoylamino, hexanoylamino, benzoylamino, etc. The amino groups substituted with an alkoxycarbonyl group, i.e. alkoxycarbonylamino groups include, for example, methoxycarbonylamino, ethoxycarbonylamino, n-propoxycarbonylamino, n-butoxycarbonylamino, tert-butoxycarbonylamino, pentyloxycarbonylamino, hexyloxycarbonylamino, etc.

The amino groups substituted with an aryloxycarbonyl group, i.e. an aryloxycarbonylamino group includes, for example, an amino group wherein one hydrogen atom of the amino group is substituted by said aryloxycarbonyl group, and specific examples are phenoxycarbonylamino, naphthyloxycarbonylamino, etc.

The amino groups substituted with an aralkyloxycarbonyl group, i.e. an aralkyloxycarbonylamino group includes, for example, benzyloxycarbonylamino, etc.

The substituted silyl groups are, for example, a tri-substituted silyl group wherein three hydrogen atoms of the silyl group are substituted with a hydrocarbon substituent such as alkyl, aryl, aralkyl, etc. which are described above for $R^1$. Specific examples of such tri-substituted silyl groups are trimethylsilyl, tert-butyldimethylsilyl, tert-butyldiphenylsilyl, triphenylsilyl, etc.

As a spacer represented by $R^2$, there are exemplified an optionally substituted alkylene group, an optionally substituted alkenylene group, an optionally substituted divalent aromatic group, an optionally substituted divalent oxyalkylene group, etc.

As an optionally substituted alkylene group, there are exemplified an alkylene group, a substituted alkylene group, etc. The alkylene group may be a linear, branched or cyclic alkylene group of 1 to 10 carbon atoms. Specific examples of said alkylene group are methylene, ethylene, propylene, trimethylene, butylenes, 2-methylpropylene, pentylene, 2,2-dimethylpropylene, 2-ethylpropylene, hexylene, heptylene, octylene, nonylene, decylene, cyclohexylene, etc.

The optionally substituted alkenylene group includes an alkenylene group and a substituted alkenylene group, and the optionally substituted alkeneylene group may be a linear, branched, or cyclic alkenylene of 2 to 10 carbon atoms. Specific examples of such alkenylene groups are vinylene, propenylene, 1-butenylene, 2-butenylene, etc.

The optionally substituted divalent aromatic group includes a divalent aromatic group and a substituted divalent aromatic group. The divalent aromatic group includes, for example, an aromatic group of 6 to 12 carbon atoms, specifically such as phenylene, biphenyldjyl, —$CH_2C_6H_5$—, —$CH_2C_6H_4CH_2$—, etc.

The optionally substituted oxyalkylene group includes an oxyalkylene group and a substituted oxyalkylene group. As the oxyalkylene group, there is exemplified an alkylene group which contains an oxygen atom at an arbitrary position in the aforementioned alkylene group. For example, there is exemplified —$((CH_2)_{n1}$—O—$(CH_2)_{n2})_{n3}$— wherein n1 to n3 are each independently a natural number, preferably 1 to 6, more preferably 1 to 3, and the alkylene group in the parenthesis may be linear or branched.

As the substituted alkylene groups, substituted alkenylene groups, substituted divalent aromatic groups and substituted oxyalkylene groups, there is exemplified each group wherein at least one hydrogen atom in the alkylene group, alkenylene group, divalent aromatic group and oxyalkylene group is substituted with the aforementioned substituent.

As these spacers, it is preferable to use a group having at least one hydrogen atom in the carbon atom adjacent to the carbonyl group capable of reacting ammonia or an amine or a salt thereof, and more preferable to use an optionally substituted alkylene group having at least one hydrogen atom in the carbon atom adjacent to the carbonyl group capable of reacting ammonia or an amine or a salt thereof.

When $R^1$ and $R^2$; $R^2$ and $R^3$; or $R^1$ and $R^3$ are taken together to form a ring, the ring may be monocyclic, polycyclic or fused ring of, for example, 4- to 8-membered ring, which ring may contain —O—, —NH—, etc. in the ring-constituent carbon chain atom. Specific examples of the ring when a ring is formed include cyclopentanones, cyclohexanones, lactones of, for example, 5- to 7-membered ring, lactams of, for example, 5- to 7-membered ring, etc.

Among keto acids of the formula (1) used in the present invention, a preferable compound can be a β-keto acid derivative of the formula (1-1):

(1-1)

wherein $R^1$, $R^3$ and $R^{11}$ have each the same meaning as defined above. Although $R^{11}$ is hydrogen, an optionally substituted hydrocarbon group, an optionally substituted alkoxy group, an optionally substituted allyloxy group, an optionally substituted aralkyloxy group or hydroxy, these groups such as "an optionally substituted hydrocarbon group", "an optionally substituted alkoxy group", "an optionally substituted allyloxy group" and "an optionally substituted aralkyloxy group" are the same with each group as mentioned for the above $R^3$.

Specific examples of the keto acid derivatives of the formula (1) used in the present invention are, for example, compounds given below.

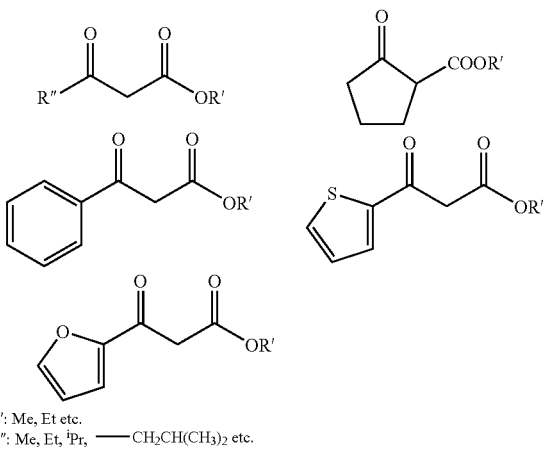

R': Me, Et etc.
R'': Me, Et, iPr, ——CH₂CH(CH₃)₂ etc.

In the formula (2), Q is a monovalent group formed by removing one hydrogen atom from ammonia or an amine.

The ammonia or amine used in the present invention can be represented, for example, by the formula (3):

(3)

wherein $R^4$, $R^5$, a and X' are each the same meaning as defined above.

The amines or salts thereof represented by the formula (3) can be ammonia when $R^4$ and $R^5$ are each hydrogen, a primary amine when one of them is hydrogen, and a secondary amine when both of them are a group other than hydrogen. In the case of secondary amine, $R^4$ and $R^5$ may be the same or different, and ammonia, primary amine and secondary amine may take the form of its salt.

The optionally substituted hydrocarbon group and the optionally substituted heterocyclic group are each the same with each group as mentioned for the above $R^1$. Also, the optionally substituted alkoxy group, the optionally substituted aryloxy group and the optionally substituted aralkyloxy group are each the same as each group of $R^3$ mentioned above.

In the case that $R^4$ and $R^5$ are combined to form a cyclic amine, the formed ring may be monocyclic, polycyclic, or fused ring, including, for example, 4-to 8-membered ring, which ring may contain —O—, —NH—, etc., in the ring-constituent carbon chain. Specific examples of such rings are pyrrolidine, piperidine, morpholine, etc.

As mentioned above, there are exemplified primary amines and secondary amines represented by the formula (3) as the amine used in the present invention. Specific examples of such amines are alkylamines such as methylamine, ethylamine, propylamine, butylamine, cyclohexylamine, etc., aralkylamines such as benzylamine, etc., cyclic amines such as pyrrolidine, piperidine, morpholine, etc., hydroxylamines such as O-benzylhydroxylamine, O-methylhydroxylkamine, etc., halogenated alkyl-substituted amines such as 1H,1H-heptafluorobutylamine, 1H,1H-tridecafluoroheptylamine, 1H,1H-pentadecafluorooctylamine, 1H,1H-heptadecafluorononylamine, etc., anilines such as aniline, 3,4-difluoroaniline, 3,5-dichloroaniline, 2,3,4-trichloroaniline, 2,4,5-trichloroaniline, 3,4,5-trichloroaniline, 2,4-dibromoaniline, 2,5-dibromoaniline, 3,4,5-tribromoaniline, 4-iodoaniline, 3-iodoaniline, 2-iodoaniline, 2-methoxyaniline, 3-methoxyaniline, 4-methyoxyaniline (also referred to as anisidine), etc., and an amine represented by the formula (3a):

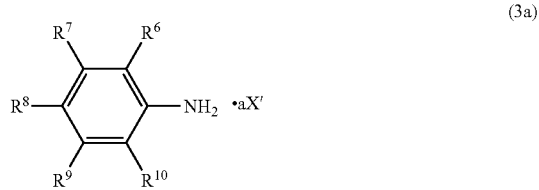

wherein $R^6$ to $R^{10}$ are each independently a hydrogen atom, an optionally substituted hydrocarbon group, a halogen atom, an optionally substituted heterocylic group, an optionally substituted alkoxy group, an optionally substituted aralkyloxy group, an optionally substituted aryloxy group, an optionally substituted acyl group, an acyloxy group, an alkoxycarbonyl group, an aryloxycarbonyl group, an aralkyloxycarbonyl group, an alkylenedioxy group, a hydroxy group, a nitro group or an optionally substituted amino group, and a and X' are each the same as mentioned above. Further, $R^6$ and $R^7$; $R^7$ and $R^8$; $R^8$ and $R^9$; or $R^9$ and $R^{10}$, taken together, form a fused ring, provided that at least one of $R^6$ to $R^{10}$ is a halogenated hydrocarbon group.

The optionally substituted hydrocarbon group, halogen atom, optionally substituted heterocyclic group, optionally substituted alkoxy group, optionally substituted aralkyloxy group, optionally substituted aryloxy group, optionally substituted acyl group, acyloxy group, alkoxycarbonyl group, aryloxycarbonyl group, aralkyloxycarbonyl group and alkylenedioxy group are each the same as mentioned above. The optionally substituted amino group includes an amino group and an optionally substituted amino group. The substituted amino groups are the same as mentioned above.

Examples of the fused ring formed when $R^6$ and $R^7$; $R^7$ and $R^8$; $R^8$ and $R^9$; or $R^9$ and $R^{10}$ are taken together are indene, naphthalene, benzofuran, indazole, quinoline, isoquinoline, etc.

Specific examples of the amines represented by the formula (3a) are 4-trifluoromethylaniline, 3-trifluoromethylaniline, 2-triifluoromethylaniline, 3,5-bis(trifluoromethyl)aniline, 2,5-bis(trifluoromethyl)aniline, 3,4,5-tris(trifluoromethyl)aniline, 4-pentafluoroethylaniline, 3-pentafluoroethylaniline, 2-pentafluoroethylaniline, 2,4-diperfluoropropylaniline, 2,3-diperfluoropropylaniline, 3,5-diperfluoropropylaniline, 2,3,4-triperfluorobutylaniline, 2,4,5-triperfluoropentylaniline, 4-perfluorohexylaniline, 4-trichloromethylaniline, 3-trichloromethylaniline, 2-trichloromethylaniline, 3,4-dipentachloroethylaniline, 4-tribromomethylaniline, 3-tribromomethylaniline, 2-tribromomethylaniline, etc.

As the secondary amine, there are exemplified dimethylamine, diethylamine, dipropylamine, diisopropylamine, dicyclohexylamine, dibenzylamine, N-methylaniline, etc.

The above-mentioned ammonia, primary amines and secondary amines may be free or their salts. As such a salt (a is 1 in the above formula (3) and (3a)), there are exemplified salts with an acid or a fluorine-containing alcohol. The acid capable of forming such a salt includes an inorganic acid, an organic acid and a Lewis acid. The inorganic acid includes, for example, hydrochloric acid, hydrobromic acid, sulfuric acid, phosphoric acid, tetrafluoroboric acid, perchloric acid, periodic acid, etc. The organic acid includes, for example, carboxylic acids (e.g. formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, glycolic acid, etc.), sulfonic acids (e.g. methanesulfonic acid, benzenesulfonic acid, p-toluenesulfonic acid, trifluoromethanesulfonic acid, etc.), and Lewis acids such as halogenated alkylaluminums (e.g. aluminum chloride, aluminum bromide, etc.), halogenated dialkylaluminums (e.g. diethylaluminum chloride, diethylaluminum bromide, diusoproylaluminum chloride, etc.), trialkoxyaluminums (e.g. triethoxyaluminum, triisopropoxyaluminum), titanium halides (e.g. titanium tetrachloride, etc.), tetraalkoxy titaniums (e.g. tetraisopropoxy titanium, etc.), halogenated borons (e.g. boron trifluoride, boron trichloride, boron tribromide, boron trifluoride-diethyl ether complex, etc.), and zinc halides (e.g. zinc chloride, zinc bromide, etc.).

With respect to fluorine-containing alcohols capable of forming a salt, there are exemplified fluorine-containing aliphatic alcohols. Examples of such alcohols are saturated or unsaturated fluorine-containing aliphatic alcohols of, for example, 2 to 10 carbon atoms. The alcohols include specifically 2,2,2-trifluoroethanol, 2,2-difluoroethanol, 3,3,3-trifluoropropanol, 2,2,3,3,3,-pentafluoropropanol, 2,2,3,3-tetrafluoropropanol, hexafluoroisopropanol, 2-methyl-3,3,3-trifluoroethanol, 3,3,4,4,4-pentafluorobutanol, 4,4,5,5,5-pentafluoropentanol, 5,5,6,6,6,-pentafluorohexanol, 3,3,4,4,5,5,6,6,6-nonafluorohexanol, 1,1,1,3,3,3-hexafluoro-2-propanol, etc. Among these fluorine-containing aliphatic alcohols, 2,2,2-trifluoroethanol, 2,2-difluoroethanol, 3,3,3-trifluoropropanol, 2,2,3,3,3,-pentafluoropropanol, 2,2,3,3-tetrafluoropropanol, hexafluoroisopropanol, 1,1,1,3,3,3-hexafluoro-2-propanol, etc. are preferable.

Here, the fluorine-containing alcohol salt of ammonia or amines include a substantial salt such as fluorine-containing alcohol solvate, though it is not present in the form of an actual salt.

In accordance with the present invention, the amino acid derivatives or their salts represented by the formula (2) can be preferably an optically active amino acid derivative or its salt of the formula (2-1):

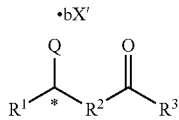

(2-1)

wherein $R^1$ to $R^3$, Q, X', b, and * have each the same meaning as mentioned above.

By using the above β-keto acid derivative of the formula (1-1) as a keto acid of the formula (1), there is obtained effectively an optically active β-amino acid derivative of the formula (2-2):

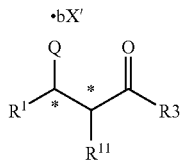

(2-2)

wherein $R^1$, $R^3$, $R^{11}$, Q, X', b and * have each the same meaning as mentioned above, provided that when $R^{11}$ is a hydrogen atom, then the carbon atom to which $R^{11}$ is attached is not a chiral carbon atom.

In the process of the present invention using a keto acid derivative (1), when an amine or a salt thereof represented by the above formula (3) as ammonia or an amine, there is obtained an amino acid derivative of the formula (2a):

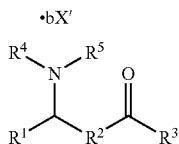

(2a)

wherein $R^1$ to $R^5$, X' and b have each the same meaning as defined above, or a salt thereof, preferably an optically active amino acid derivative or a salt thereof represented by the formula (2a-1):

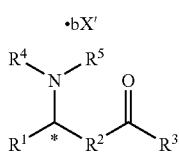

(2a-1)

wherein $R^1$ to $R^5$, X', b and * have each the same meaning as defined above.

Further, when an amine of the formula (3a) is employed as an amine, there is obtained an amino acid derivative of the formula (2b):

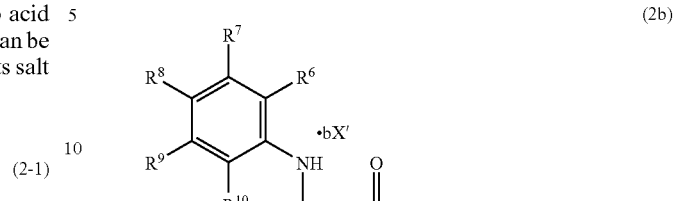

(2b)

wherein $R^1$ to $R^3$, $R^6$ to $R^{10}$, X' and b have each the same meaning as defined above, preferably an optically active amino acid derivative of the formula (2b-1):

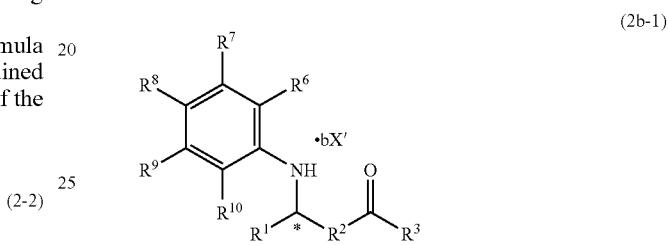

(2b-1)

wherein $R^1$ to $R^3$, $R^6$ to $R^{10}$, b, X' and * have each the same meaning as defined above.

Examples of the amino acid derivatives (2) obtained by the process of the present invention are β-amino acid derivatives including methyl 3-aminopentanoate, methyl 3-aminobutanoate, 3-aminopentanoic acid, methyl 3-amino-3-thiophen-2-yl-propionate, methyl 3-amino-3-thiophen-3-yl-propiionate, methyl 3-amino-3-furan-2-yl-propionate, 3-amino-3-furan-3-yl-propionate, ethyl 3-amino-3-phenylpropionate, methyl 3-(benzylamino)butanoate, methyl 3-(4-trifluoromethylphenylamino)-pentanoate, ethyl 3-amino-5-methyl-hexanoate, methyl 2-amino-cyclopentanecarboxylate, 3-(4-trifluoromethylanilino)butyryl-1,3-oxazolidin-2-one, 3-(2-trifluoromethylanilino)butyryl-1,3-oxazolidin-2-one, 3-(4-trifluoromethylanilino)butyryl-1,3-oxazolidin-2-one, 3-[3-(4-trifluoromethyl-2-methoxy-phenylamino)butyryl]-oxazolidinone, 3-(4-trifluoromethylanilino)pentenoic acid methylcarbamate, 3-(4-trifluoromethylanilino)pentenoyl-1,3-oxazolidin-2-one, 3-(3-phenylaminobutyryl)-oxazolidin-2-one, etc., and especially optically active compounds thereof. It should be understood that the present invention is not restricted to these compounds.

By carrying out the process of the present invention in the presence of a chiral catalyst under hydrogen gas, there is obtained an optically active amino acid derivative among amino acid derivatives of the formula (2), effectively in a good enantiomeric yield.

As the chiral catalyst, there is preferably used a transition metal complex. Among those complexes of the transition metals, the complexes of the metals of the Groups 8 to 10 in the periodic table are preferable.

Examples of such transition metal complex include, for example, compounds of the formula (7) or (8):

$$M_m L_n X_p Y_q \qquad (7)$$

$$[M_m L_n X_p Y_q]Z_s \qquad (8)$$

wherein M is a transition metal of the Groups 8 to 10 in the periodic table, L is a chiral ligand, X is a halogen atom, a carboxylato group, an allyl group, 1,5-cyclooctadiene or norbornadiene, Y is a ligand, Z is an anion or a cation, and m, n, p, q, and s are each an integer of 0 to 5.

The transition metals of the Groups 8 to 10 in the periodic table, represented by M in the formulae (7) and (8), are each the same or different and include ruthenium (Ru), rhodium (Rh), iridium (Ir), palladium (Pd), nickel (Ni), etc.

The chiral ligand represented by L may be the same or different monodentate or bidentate ligand. Preferable chiral ligand includes an optically active phosphine ligand, and an optically active bidentate phosphine ligand is more preferable.

Specific examples of such chiral ligand include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane(SKEWPHOS), 1,2-bis(substituted phospholano)benzene (DuPHOS), 1,2-bis(substituted phospholano)ethane (BPE), 1-(substituted phospholano)-2-(diphenylphosphino)benzene (UCAP-Ph), 1-(bis(3,5-dimethylphenyl)phosphino)-2-(substituted phospholano)benzene (UCAP-DM), 1-(substituted phospholano)-2-(bis(3,5-di(t-butyl)-4-methoxyphenyl)phosphino)benzene (UCAP-DTBM), 1-(substituted phospholano)-2-(di-naphthalen-1-yl-phosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octa-hydrobinaphthyl) ($H_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6),(5',6')-bis(methylenedioxy)biphenyl-2,2'-diyl)(bisdiphenylphosphine) (SEGPHOS), ((5,6),(5',6')-bis(methylenedioxy)biphenyl-2,2'-diyl)(bis(3,5-dimethylphenyl)phosphine) (DM-SEGPHOS), ((5,6),(5',6')-bis(methylenedioxy)biphenyl-2,2'-diyl)(bis(3,5-di(tert-butyl)-4-methoxyphenyl)phosphine) (DTBM-SEGPHOS), etc.

The ligands represented by Y are each, the same or different, neutral ligands such as aromatic compounds and olefinic compounds, amines and the like. Examples of the aromatic compound include benzene, p-cymene, 1,3,5-trimethylbenzene (mesitylene), hexamethylbenzene, etc.; examples of the olefinic compound include ethylene, 1,5-cyclooctadiene, cyclopentadiene, norbornadiene, etc.; and examples of the other neutral ligand include N,N-dimethylformamide (DMF), acetonitrile, benzonitrile, acetone, chloroform, etc.

Examples of the amines include diamines such as 1,2-diphenylethylenediamine (DPEN), 1,2-cyclohexylethylenediamine, 1,2-diaminocyclohexane, ethylenediamine, 1,1-bis(4-methoxyphenyl)-2-isopropylethylenediamine (DAIPEN), and the like, an aliphatic amines such as triethylamine and the like, and an aromatic amines such as pyridine and the like.

Halogen atom represented by X includes chlorine atom, bromine atom and iodine atom.

In the formula (8), Z represents an anion or a cation. Examples of Z anion include $BF_4$, $ClO_4$, OTf, $PF_6$, $SbF_6$, $BPh_4$, Cl, Br, I, $I_3$, sulfonate, etc., wherein Tf means triflate group ($SO_2CF_3$).

The cation can be represented, for example by the following formula: $[(R)_2NH_2]^+$ wherein a couple of R are each, the same or different, a hydrogen atom or an optionally substituted hydrocarbon group.

In the above formula, the optionally substituted hydrocarbon groups represented by R is the same as the aforementioned optionally substituted hydrocarbon group. The optionally substituted hydrocarbon group represented by R can be preferably an alkyl group of 1 to 5 carbon atoms, a cycloalkyl group, an optionally substituted phenyl group or an optionally substituted benzyl group.

Specific examples of the cation of the above formula include, for example, $[Me_2NH_2]^+$, $[Et_2NH_2]^+$, $[Pr_2NH^2]+$, etc.

The following is the detailed explanation about preferable embodiments of the aforementioned transition metal complexes.

(1) Formula (7),

$$M_mL_nX_pY_q \qquad (7)$$

1) When M is Ir or Rh, X is Cl, Br or I, and when L is a monodentate ligand, then m=p=2, n=4 and q=0; and when L is a bidentate ligand, then m=n=p=2 and q=0.
2) When M is Ru, (i) X is Cl, Br, or I, and Y is a trialkylamino group, and when L is a monodentate ligand, then m=2, n=p=4 and q=1; and when L is a bidentate ligand, then m=n=2, p=4 and q=1.
   (ii) X is Cl, Br or I, and Y is a pyridyl group or a ring-substituted pyridyl group, and when L is a monodentate ligand, then m=1, n=p=2 and q=2; and when L is a bidentate ligand, then m=n=1, p=2 and q=2, and
   (iii) X is a carboxylato group, and when L is a monodentate ligand, then m=1, n=p=2, and q=0; and when L is a bidentate ligand, then m=n=1, p=2, and q=0, and
   (iv) X is Cl, Br or I, and when L is a monodentate ligand, then m=p=2, n=4 and q=0; and when L is a bidentate ligand, then m=n=p=2 and q=0.
3) When M is Pd, (i) X is Cl, or I, and when L is a monodentate ligand, then m=1, n=2, p=2 and q=0; and when L is a bidentate ligand, then m=n=1, p=2 and q=0.
   (ii) X is an allyl group, and when L is a monodentate ligand, then m=p=2, n=4 and q=0; and when L is a bidentate ligand, then m=n=p=2 and q=0.
4) When M is Ni, X is Cl, Br or I, and when L is a monodentate ligand, m=1, n=2, p=2 and q=0; and when L is a bidentate ligand, m=n=1, p=2 and q=0.

(2) Formula (8),

$$[M_mL_nX_pY_q]Z_s \qquad (8)$$

1) When M is Ir or Rh, X is 1,5-cyclooctadiene or norbornadiene, Z is $BF_4$, $ClO_4$, OTf, $PF_6$, $SbF_6$ or $BPh_4$, m=n=p=s=1 and q=0, or m=s=1, n=2 and p=q=0.
2) When M is Ru, (i) X is Cl, Br or I, Y is a neutral ligand such as an aromatic compound and an olefinic compound and Z is Cl, Br, I, $I_3$ or sulfonate, and when L is a monodentate ligand, then m=p=s=q=1 and n=2; and when L is a bidentate ligand, then m=n=p=s=q=1.
   (ii) Z is $BF_4$, $ClO_4$, OTf, $PF_6$, $SbF_6$ or $BPh_4$, and when L is a monodentate ligand, then m=1, n=2, p=q=0 and s=2; and when L is a bidentate ligand, then m=n=1, p=q=0 and s=2.

3) When M is Pd or Ni, (i) Z is $BF_4$, $ClO_4$, OTf, $PF_6$, $SbF_6$ or $BPh_4$ and when L is a monodentate ligand, then m=1, n=2, p=q=0, s=2; and when L is a bidentate ligand, then m=n=1, p=q=0 and s=2.

These transition metal complexes can be produced by using conventional methods.

In the formulae of the transition metal complexes given below, the meanings of the symbols used are as follows, L: a chiral ligand; cod: 1,5-cyclooctadiene; nbd: norbornadiene; Tf: a triflate group ($SO_2CF_3$); Ph: phenyl group; and Ac: acetyl group. As specific examples of such transition metal complexes, only the transition metal complexes in which bidentate ligands are used as the chiral ligand are shown in order to avoid complication.

Rhodium Complex:

The rhodium complex can be produced according to the method described in "JIKKEN KAGAKU KOZA, $4^{th}$ Ed., Volume 18, Organic Metal Complexes, pp. 339-344, published by Maruzen, in 1991". More specifically, rhodium complex can be produced by reactingbis(cycloocta-1,5-diene)rhodium(I) tetrafluoroboric acid with a chiral ligand.

Specific examples of the rhodium complex include, for example, those given below:
[Rh(L)Cl]$_2$, [Rh(L)Br]$_2$, [Rh(L)I]$_2$, [Rh(cod)(L)]BF$_4$, [Rh(cod)(L)]ClO$_4$, [Rh(cod)(L)]PF$_6$, [Rh(cod)(L)]BPh$_4$, [Rh(cod)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(nbd)(L)]OTf, [Rh(L)$_2$]ClO$_4$, [Rh(L)$_2$]PF$_6$, [Rh(L)$_2$]OTf and [Rh(L)$_2$]BF$_4$.

Ruthenium Complex:

The ruthenium complex can be obtained according to the method described in the literature (T. Ikariya, Y. Ishii, H. Kawano, T. Arai, M. Saburi, S. Yoshikawa, and S. Akutagawa, J. Chem. Soc., Chem. Commun., 1985, 922) and in other literatures. More specifically, the ruthenium complex can be produced by heating [Ru(cod)Cl$_2$]n and a chiral ligand under reflux in toluene as solvent in the presence of triethylamine.

The ruthenium complex can be also produced according to the method described in the literature (K. Mashima, K. Kusano, T. Ohta, R. Noyori, H. Takaya, J. Chem. Soc., Chem. Commun., 1989, 1208). More specifically, the ruthenium complex can be obtained by heating [Ru(p-cymene)I$_2$]$_2$ and the chiral ligand in methylene chloride and ethanol with stirring. Specific examples of such ruthenium complex include, for example, those given below:
Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$, Ru(OCOCF$_3$)$_2$(L), [{RuCl(L)$_2$}(μ-Cl)$_3$][Me$_2$NH$_2$], {RuCl(L)$_2$}(μ-Cl)$_3$][Et$_2$NH$_2$], {RuBr(L)$_2$}(μ-Cl)$_3$][Me$_2$NH$_2$], {(RuBr(L)$_2$}(μ-Cl)$_3$][Et$_2$NH$_2$], RuCl$_2$(L), RuBr$_2$(L), RuI$_2$(L), RuCl$_2$(L)(diamine), RuBr$_2$(L) (diamiine), RuI$_2$(L)(diamine), [{RuI(L)}$_2$(μ-I)$_3$][Me$_2$NH$_2$], [{RuI(L)}$_2$(μ-I)$_3$][Et$_2$NH$_2$], RuCl$_2$(L)(pyridine), RuBr$_2$(L)(pyridine) and RuI$_2$(L)(pyridine).

Iridium Complexes:

The iridium complex can be obtained according to the method described in the literature (K. Mashima, T. Akutagawa, X. Zhang, T. Taketomi, H. Kumobayashi, S. Akutagawa, J. Organomet. Chem., 1992, 428, 213) and other literatures. More specifically, the iridium complex can be obtained by reacting a chiral ligand with [Ir(cod)(CH$_3$CN)$_2$]BF$_4$ in tetrahydrofuran with stirring.

Specific examples of the iridium complexes include, for example, those given below:
[Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$, [Ir(nbd)(L)]OTf.

Palladium Complexes:

The palladium complex can be obtained according to the method described in the literature (Y. Uozumi and T. Hayashi, J. Am. Chem. Soc., 1991, 9887) and in others. More specifically, they can be obtained by reacting a chiral ligand with π-allylpalladium chloride.

Specific examples of the palladium complex include, for example, those which follow: PdCl$_2$(L), (π-allyl)Pd(L), [Pd(L)]BF$_4$, [Pd(L)]ClO$_4$, [Pd(L)]PF$_6$, [Pd(L)]BPh$_4$ and [Pd(L)]OTf.

Nickel Complexes:

The nickel complex can be obtained according to the method described in "JIKKEN KAGAKU KOZA, $4^{th}$ Ed., Volume 18, Organic Metal Complexes, p. 376, published by Maruzen, in 1991" and in other literatures. The nickel complex can also be obtained, according to the method described in the literature (Y. Uozumi and T. Hayashi, J. Am. Chem. Soc., 1991, 113, 9887), by dissolving a chiral ligand and nickel chloride in a mixture of 2-propanol and methanol and heating the resultant solution with stirring.

Specific examples of the nickel complex include, for example, those which follow: NiCl$_2$(L), NiBr$_2$(L) and NiI$_2$(L).

Further, these transition metal complexes can be obtained by reacting the chiral ligand with a transition metal compound.

The transition metal compound represented by the following formula: $[MX_mL_n]_p$ wherein M, X, L, m, n and p are each the same meaning as defined above.

As the above formula, concrete examples of Ru, Rh and Ir are exemplified. Specific examples of the above formula include, for example, [RuCl$_2$(benzene)]$_2$, [RuBr$_2$(benzene)$_2$, [RuI$_2$(benzene)]$_2$, [RuCl$_2$(p-cymene)]$_2$, [RuBr$_2$(p-cymene)]$_2$, [RuI$_2$(p-cymene)]$_2$, RuCl$_2$(hexamethylbenzene)]$_2$, [RuBr$_2$(hexamethylbenzene)]$_2$, [RuI$_2$(hexamethylbenzene)]$_2$, [RuCl$_2$(mesitylene)]$_2$, [RuBr$_2$(mesitylene)]$_2$, [RuI$_2$(mesitylene)]$_2$, [RuCl$_2$(pentamethylcyclopentadiene)]$_2$, [RuBr$_2$(pentamethylcyclopentadiene)]$_2$, [RuI$_2$(pentamethylcyclopentadiene)]$_2$, [RuCl$_2$(cod)]$_2$, [RuBr$_2$(cod)]$_2$, [RuI$_2$(cod)]$_2$, [RuCl$_2$(nbd)]$_2$, [RuBr$_2$(nbd)]$_2$, [RuI$_2$(nbd)]$_2$, RuCl$_3$ hydrate, RuBr$_3$ hydrate, RuI$_3$ hydrate, [RhCl$_2$(cyclopentadiene)]$_2$, [RhBr$_2$(cyclopentadiene)]$_2$, [RhI$_2$(cyclopentadiene)]$_2$, [RhCl$_2$ (pentamethylcyclopentadiene)]$_2$, [RhBr$_2$(pentamethylcyclopentadiene)]$_2$, [RhI$_2$(pentamethylcyclopentadiene)]$_2$, [RhCl(cod)]$_2$, [RhBr(cod)]$_2$, [RhI(cod)]$_2$, [RhCl(nbd)]$_2$, [RhBr(nbd)]$_2$, [RhI(nbd)]$_2$, RhCl$_3$ hydrate, RhBr$_3$ hydrate, RhI$_3$ hydrate, [IrCl$_2$(cyclopentadiene)]$_2$, [IrBr$_2$(cyclopentadiene)]$_2$, [IrI$_2$(cyclopentadiene)]$_2$, [IrCl$_2$(pentamethylcyclopentadiene)]$_2$, [IrBr$_2$(pentamethylcyclopentadiene)]$_2$, [IrI$_2$(pentamethylcyclopentadiene)]$_2$, [IrCl(cod)]$_2$, [IrBr (cod)]$_2$, [IrI(cod)]$_2$, [IrCl(nbd)]$_2$, [IrBr(nbd)]$_2$, [IrI (nbd)]$_2$, IrCl$_3$ hydrate, IrBr$_3$ hydrate, IrI$_3$ hydrate.

As the transition metal complexes, both commercially available products and those synthesized in-house can be used. In the case of using the complex as the catalyst, the complex may be used after increasing its purity or the complex may be used without purification (in situ).

Among the transition metal complexes which can be used in the present invention, those which have chiral ligands are preferably used, and, furthermore, those which have chiral phosphine ligands as the chiral ligands mentioned above are used more preferably.

In the production of the present invention, the amount used of the chiral catalyst depends on the keto acid derivatives of the above formula (1), the reaction vessel used, the reaction mode and the production cost, it is usually appropriate to select from the range of $1/10$ to $1/100,000$ in mole or preferably from the range of $1/50$ to $1/10,000$ in mole against the keto acid derivative used.

The reaction between the keto acid derivative of the above formula (1) and ammonia or an amine or a salt thereof in a hydrogen stream in accordance with the present invention is preferably carried out in the presence or absence of an acid and/or a fluorine-containing alcohol. Here, when the free ammonia or free amine is used, the reaction is conducted in the presence of an acid and/or a fluorine-containing alcohol if necessary. Further, when a salt of ammonia or that of an amine is used, the reaction is not necessarily carried out in the presence of an acid and/or a fluorine-containing alcohol, however, the reaction may be conducted in the presence of an acid and/or a fluorine-containing alcohol depending on the necessity.

The acid suitably used in the method of the present invention includes an inorganic acid, an organic acid and a Lewis acid and so on.

Examples of the inorganic acid include, for example, hydrochloric acid, hydrobromic acid, sulfuric acid, phosphoric acid, tetrafluoroboric acid, perchloric acid, periodic acid, etc. The organic acid includes, for example, a carboxylic acid (e.g. formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, glycolic acid, etc.), and a sulfonic acid (e.g. methanesulfonic acid, benzenesulfonic acid, p-toluenesulfonic acid, trifluoromethanesulfonic acid, etc.). As the Lewis acid, there are mentioned halogenated aluminums (e.g. aluminum chloride, aluminum bromide, etc.), halogenated dialkylaluminums (e.g. diethylaluminum chloride, diethylaluminum bromide, diisoproylaluminum chloride, etc.), trialkoxy aluminums (e.g. triethoxyaluminum, triiusopropoxyaluminum, tri-t-butoxy-aluminum), titanium halides (e.g. titanium tetrachloride, etc.), tetraalkoxy titaniums (e.g. tetraisopropoxy titanium, etc.), halogenated borons (e.g. bron trifluoriide, boron trichloride, boron tribromide, boron trifluoride-diethyl ether complex, etc.), zinc halides (e.g. zinc chloride, zinc bromide, etc.). Each of these acids may be used alone or appropriately in combination of two or more kinds of them.

The amount of the acid used is usually selected appropriately from the range of 0.1 to 10 equivalents, preferably 0.5 to 3 equivalents, to the keto acid derivative.

The fluorine-containing aliphatic alcohol includes, for example, a saturated or unsaturated fluorine-containing aliphatic alcohol of 2 to 10 carbon atoms. Specific examples of the fluorine-containing aliphatic alcohol include, for example, 2,2,2-trifluoroethanol, 2,2-difluoroethanol, 3,3,3-trifluoropropanol, 2,2,3,3,3-pentafluoropropanol, 2,2,3,3-tetrafluoropropanol, hexafluoroisopropanol, 2-methyl-3,3,3-trifluoroethanol, 3,3,4,4,4-pentafluorobutanol, 4,4,5,5,5-pentafluoropentanol, 5,5,6,6,6-pentafluorohexanol, 3,3,4,4,5,5,6,6,6-nonafluorohexanol, 1,1,1,3,3,3-hexafluoro-2-propanol, etc. Each of these fluorine-containing alcohols may be used alone or appropariately in combination of two or more these solvents. Among these fluorine-containing alcohols, 2,2,2-trifluoroethanol, 2,2-difluoroethanol, 3,3,3-trifluoropropanol, 2,2,3,3,3-pentafluoropropanol, 2,2,3,3-tetrafluoropropanol, hexafluoroisopropanol 1,1,1,3,3,3-hexafluoro-2-propanol and the like are preferable.

The amount of the fluorine-containing alcohol to be used is 0.1 to 50 equivalents, preferably 0.5 to 10 equivalents, to the keto acid derivative.

The amount used in combination of the acid with the fluorine-containing keto acid derivative is usually selected appropriately from the range of 0.1 to 20 equivalents, preferably 0.5 to 10 equivalents, to the keto acid derivative.

The mixing ratio of the acid and the fluorine-containing alcohol is usually 10:1 to 1:10, preferably 5:1 to 1:5.

The process of the present invention may be carried out in a solvent, if necessary. Said solvent may be employed, depending on the kind of the keto acid derivative of the formula (1), ammonia or the amine or a salt thereof, and the acid and the fluorine-containing alcohol optionally used. When said amine, acid, and fluorine-containing alcohol can be served as a solvent, it is not necessary to use other solvents.

It is preferable to use a solvent capable of dissolving the keto acid of the formula (1) and the chiral hydrogenation catalyst.

The solvents include, for example, aromatic hydrocarbons (e.g. benzene, toluene, xylene, etc.), aliphatic hydrocarbons (e.g. pentane, hexane, heptane, octane, etc.), halogenated hydrocarbons (e.g. methylene chloride, chloroform, carbon tetrachloride, dichloroethane, etc.), ethers (e.g. diethyl ether, diisopropyl ether, tert-butyl methyl ether, dimethoxyethane, tetrahydrofuran, dioxane, dioxolane, etc.), alcohols (e.g. methanol, ethanol, 2-propanol, n-butanol, tert-butanol, benzyl alcohol, etc.), polyalcohols (e.g. ethylene glycol, propylene glycol, 1,2-propanediol, glycerin, etc.), amides (e.g. N,N-dimethylformamide, N,N-dimethylacetamide, etc.), acetonitrile, N-methylpyrrolidone, dimethyl sulfoxide, etc. These solvents may be used solely or appropariately in combination with two or more kinds of solvents. Among these solvents, methanol, ethanol, 2-propanol, n-butanol, tert-butanol and benzyl alcohol, and the like are preferable.

The amount of the solvent used can be determined in view of solubility and economical cost of the keto acid derivative which is a reaction substrate. For example, when an alcohol is used as a solvent, it is possible to carry out the reaction at a concentration of from not more than 1% to in the absence of a solvent or in the almost absence of a solvent. Usually, the concentration of the keto acid is selected appropriately from the range of 1 to 200% by mass, preferably 10 to 100% by mass.

The hydrogen pressure in the process of the present invention is sufficient in such a condition of hydrogen atmosphere or 0.1 MPa, however, it is usually selected from the range of 0.01 to 20 MPa, preferably 0.1 to 10 MPa in view of economical cost. Further, it is possible to maintain high activity even at a pressure of not higher than 1 MPa in view of economical cost.

In the process of the present invention, the starting keto acid derivative, ammonia or amine or a salt thereof and hydrogen gas can be supplied simultaneously in the reaction system, or hydrogen gas may be supplied after feed of the keto acid derivative, ammonia, amine or a salt thereof.

The process of the present invention may be carried out in the presence of a dehydrating agent. Examples of such dehydrating agent are solid oxides (e.g. silica gel, alumina, silica alumina, etc.), inorganic dehydrating agents (e.g. conc. sulfuric acid, phosphorous pentoxide, anhydrous zinc chloride, etc.), acid anhydrides (e.g. acetic anhydride, etc.), carbonyldiimidazole, p-tolenesulfonyl chloride, zeolites (e.g. molecular sieves 3A, 4A, etc.), (anhydrous) inorganic salts (e.g.

anhydrous calcium chloride, anhydrous calcium sulfate, anhydrous magnesium chloride, anhydrous magnesium sulfate, anhydrous potassium carbonate, anhydrous potassium sulfide, anhydrous potassium sulfite, anhydrous sodium sulfate, anhydrous sodium sulfite, anhydrous copper sulfate, etc.), heteropolyacids (more than one water molecule may be added to heteropolyacid, or heteropolyacid may be deposited on a carrier) (e.g. $H_3PW_{12}O_{40}$, $H_3PW_{11}MoO_{40}$, $H_3PW_{10}Mo_2O_{40}$, $H_3PW_9Mo_3O_{40}$, $H_3PW_8Mo_4O_{40}$, $H_3PVW_{11}O_{40}$, $H_3PV_2W_{10}O_{40}$, $H_3PV_3W_9O_{40}$, $H_3PV_4W_8O_{40}$, $H_4SiW_{12}O_{40}$, $H_4SiW_{11}MoO_{40}$, $H_4SiW_{10}Mo_2O_{40}$, $H_4SiW_9Mo_3O_{40}$, $H_4SiW_8Mo_4O_{40}$, $H_4SiVW_{11}O_{40}$, $H_4SiV_2W_{10}O_{40}$, $H_4SiV_3W_9O_{40}$, $H_4SiV_4W_8O_{40}$, etc.), cation-exchange resins (e.g. styrene sulfonic acid type, phenol sulfonic acid type, fluorinated alkylsulfonic acid type, etc.) and the like.

Specific examples of the cation-exchange resin include Amberlyst 15 (registered trademark), Amberlyst 16 (registered trademark) Amberlyst 36 (registered trademark), Amberlite XE-284 (registered trademark) (all these Amberlysts are products of Rohm & Haas), Nafion (registered trademark) (Product of E. I. DuPont), etc. A cation-exchange resin may be deposited on a carrier. The carrier includes silica, etc.

The amount of the dehydration agent is usually selected appropriately from the range of 0.1 to 5.0 equivalents or preferably from the range of 0.5 to 2.0 equivalents to that of the keto acid derivative of the formula (1).

Usually, the reaction temperature is selected appropriately from the range of 15 to 120° C., preferably 20 to 100° C. in view of economical cost. Further, it is possible to carry out the reaction even at a low temperature of −30 to 0° C. or a high temperature of 100 to 250° C.

Usually, the reaction time is selected appropriately from the range of one minutes to several days, preferably 10 minutes to 48 hours, more preferably 10 minutes to 24 hours, though it varies with the reaction conditions such as the kinds and amounts of the chiral hydrogenation catalysts used, the kinds and concentrations of the keto acid derivative of the formula (1), amine or a salt thereof, the reaction temperature, and the hydrogen pressure.

The process of the present invention may be carried out by a batch-method or a continuous method.

In the case that the amino acid derivative of the formula (2) thus obtained is a free amino acid derivative, it may be converted into a salt of said amino acid derivative if required, i.e. a salt of said amino acid derivative with an acid and/or a fluorine-containing alcohol. Such acid and/or fluorine-containing alcohol is/are the same as described above. Further, in the case that the amino acid derivative of the formula (2) is a salt of said amino acid derivative, such salt may be converted, if necessary, into another salt by exchanging the acid and/or the fluorine-containing alcohol capable of forming a salt.

EXAMPLES

The present invention is illustrated in more detail by referring to the following Examples. However, the present invention is in no way restricted by these examples.

Apparatuses used in the following Examples for measuring physical constants are as follows:

Nuclear Magnetic Resonance:
(1) DRX500 (BRUKER JAPAN CO. LTD.) $^1$H-NMR (500.13 MHz), $^{13}$C-NMR (125.76 MHz).
(2) Gemini 2000 (Varian) $^1$H-NMR (200 MHz)
Gas Chromatography (GLC): Hewlett Packard 5890-II High Performance Liquid Chromatography (HPLC): Shimadzu Seisakusho LC10OAT & SPD10A Mass Spectrum (MASS): Hitachi M-80B Measurement of Enantiomeric Excess:

Enantiomeric excess of an amine having an unsubstituted amino group is, for example, determined as follows:

The resulting amine is acylated with, for example, acetic anhydride or 4-nitrobenzoyl chloride in the presence of a base such as triethylamine to yield an acetylated compound of the formula (9):

wherein $R^x$ is a protecting group such as acyl, etc; $R^1$, $R^2$, $R^3$ and * have each the same meaning as defined above. The enantiomeric excess of the above acylated compound is determined by gas chromatography (GLC) using a chiral capillary column such as a CP-Chirasil DEX-CB (available from CHROMPACK CO.) or high performance liquid chromatography (HPLC) using a chiral column such as a CHIRALCEL OD-H column (available from by DAICEL CHEMICAL INDUSTRIES, LTD.).

Example 1

Synthesis of methyl (3R)-3-aminobutanoate p-toluenesulfonate

Ru(OCOCH$_3$)$_2$((R)-dm-binap) (164.3 mg, 0.1722 mmol), methyl acetoacetate (10.00 g, 86.12 mmol), ammonium acetate (6.64 g, 86.12 mmol) and methanol (50 mL) were placed in a stainless steel autoclave under nitrogen atmosphere, and the mixture was stirred at 80° C. under a hydrogen pressure of 3 MPa for 15 hours. After completion of the reaction, the solvent was removed by evaporation to give methyl (3R)-3-aminobutanoate acetate as a crude material (16.29 g). The crude product was treated with 7N ammonia/methanol and analyzed by GLC analysis using a capillary column TC-5HT (available from GL SCIENCES CO.), indicating that the yield of methyl 3-aminobutanoate was 86.4%, that of the by-produced methyl 3-hydroxybutanoate was 0.7%, that of the by-produced methyl 3-aminocrotonate was 1.4% and that of the by-produced methyl 3-(2-methoxycarbonyl-1-methyl-ethylamino)-2-butenoate was 6.2%. The enantiomeric excess of methyl (3R)-3-aminobutanoate in the crude product was found to be 81.9% ee by HPLC analysis using a CHIRALCEL OD-H column after conversion into methyl (3R)-3-(4-nitrobenzoylamino)butanoate.

The resulting crude material (16.29 g) was dissolved in methyl acetate (25 mL), and to the solution was added dropwise a solution of p-toluenesulfonic acid monohydrate (16.38 g; 86.12 mmol) in methyl acetate (100 mL) at room temperature over a period of 30 minutes. The mixture was stirred at room temperature for one hour and cooled down to −10° C. to precipitate a solid. The solid was collected by filtration to give methyl (3R)-3-aminobutanoate p-toluenesulfonate (18.25 g, white crystal) in 73.2% yield. The enantiomeric excess of the product obtained above was determined to be 91.7% ee after conversion into methyl (3R)-3-(4-nitrobenzoylamino)butanoate in a similar manner to the crude product.

$^1$H-NMR(DMSO-d$_6$): δ; 1.20 (d, J=6.6 Hz, 3H), 2.28 (s, 3H), 2.56 (dd, J=7.4, 16.8 Hz, 1H), 2.68 (dd, J=6.3, 16.8 Hz, 1H), 3.40-3.60 (m, 1H), 3.63 (s, 3H), 7.12 (d, J=8.0 Hz, 2H), 7.49 (d, J=8.0 Hz, 2H), 7.83 (brs, 3H).

Examples 2 to 19

Except for changes of the catalyst, the amount of methanol, the reaction temperature, the reaction time, the molar ratio of the metal in the catalyst and the molar ratio of the additive used in Example 1, the same reaction as in Example 1 was carried out using methyl acetoacetate as a starting material, as shown in Table 1. The yield of methyl 3-aminobutanoate was analyzed by GLC analysis using a capillary column TC-5HT after treatment of the crude product with 7N ammonia/methanol obtained in the same way as in Example 1. The enantiomeric excess was determined by HPLC analysis using a CHIRALCEL OD-H column after conversion into methyl (3R)-3-(4-nitrobenzoylamino)butanoate in a similar manner to Example 1. The reaction results are shown in Table 1.

TC-5HT, indicating that the yield of methyl 3-aminobutanoate was 87.2%, that of the by-produced methyl 3-hydroxybutanoate was 0.3%, that of the by-produced methyl 3-aminocrotonate was 0.4% and that of the by-produced methyl 3-(2-methoxycarbonyl-1-methyl-1-ethylamino)-2-butenoate was 6.6%. The enantiomeric excess of methyl(3R)-3-aminobutanoate in the crude product was determined to be 94.4% ee by HPLC analysis using a CHIRALCEL OD-H column after conversion into methyl (3R)-3-(4-nitrobenzoylamino) butanoate.

The resulting crude material (161.20 g) was dissolved in methyl acetate (250 mL), and to the solution was added dropwise a solution of p-toluenesulfonic acid monohydrate (137.05 g, 0.721 mol) in methyl acetate (500 mL) at 50° C. over a period of 30 minutes. The mixture was stirred at room

TABLE 1

| Example | Catalyst[a] | Substrate/ Catalyst (Molar ratio) | Methanol/ Substrate (mL/g) | Reaction temperature (° C.) | Reaction time (h) | Additive/ Methyl acetoacetate (Molar Ratio) | Yield[b] (%) | Enantiomeric excess[c] (% ee) |
|---|---|---|---|---|---|---|---|---|
| 2 | A | 200 | 5 | 80 | 15 | $CH_3CO_2NH_4$ (1.0) | 76.7 | 82.3 (R) |
| 3 | A | 500 | 5 | 80 | 15 | $CH_3CO_2NH_4$ (1.0) | 55.3 | 84.1 (R) |
| 4 | A | 500 | 5 | 90 | 7 | $CH_3CO_2NH_4$ (1.0) $CH_3CO_2H$ (2.0) | 94.2 | 83.9 (R) |
| 5 | B | 500 | 5 | 80 | 15 | $CH_3CO_2NH_4$ (1.0) $CF_3CH_2OH$ (1.0) | 87.3 | 87.2 (R) |
| 6 | B | 500 | 5 | 80 | 15 | $CH_3CO_2NH_4$ (2.0) | 30.1 | 83.7 (R) |
| 7 | B | 500 | 5 | 80 | 15 | $HCO_2NH_4$ (1.0) | 7.5 | 86.5 (R) |
| 8 | B | 1,000 | 5 | 80 | 15 | $CH_3CO_2NH_4$ (1.0) | 69.1 | 47.6 (R) |
| 9 | B | 1,000 | 5 | 80 | 15 | $CH_3CO_2NH_4$ (1.2) | 26.7 | 84.7 (R) |
| 10 | B | 1,000 | 5 | 80 | 15 | $CH_3CO_2NH_4$ (1.0) $CH_3CO_2H$ (0.1) | 36.2 | 88.0 (R) |
| 11 | B | 1,000 | 5 | 80 | 15 | $CH_3CO_2NH_4$ (1.0) $CH_3CO_2H$ (1.0) | 80.7 | 51.6 (R) |
| 12 | B | 1,000 | 5 | 80 | 15 | $CH_3CO_2NH_4$ (1.0) $MgSO_4$ (1.0) | 37.2 | 91.5 (R) |
| 13 | B | 1,000 | 5 | 80 | 15 | $CH_3CO_2NH_4$ (1.0) $CF_3CH_2OH$ (1.0) | 44.8 | 89.6 (R) |
| 14 | C | 1,000 | 5 | 80 | 15 | $CH_3CO_2NH_4$ (1.0) | 48.6 | 35.8 (R) |
| 15 | D | 1,000 | 5 | 80 | 15 | $CH_3CO_2NH_4$ (1.0) | 11.2 | 85.4 (R) |
| 16 | E | 500 | 10 | 80 | 7 | $CH_3CO_2NH_4$ (1.0) | 74.6 | 91.8 (R) |
| 17 | E | 700 | 5 | 90 | 8 | $CH_3CO_2NH_4$ (1.0) $CH_3CO_2H$ (1.2) | 94.6 | 92.2 (R) |
| 18 | E | 1,000 | 10 | 90 | 8 | $CH_3CO_2NH_4$ (1.0) $CH_3CO_2H$ (2.0) | 92.6 | 92.9 (R) |
| 19 | F | 500 | 5 | 80 | 15 | $CH_3CO_2NH_4$ (1.0) | 77.4 | 66.0 (R) |

[a]A: $Ru(OAc)_2((R)$-tol-binap), B: $Ru(OAc)_2((R)$-dm-binap), C: $Ru_2Cl_4((R)$-dm-binap$)_2NEt_3$, D: [RUCl(p-cymene)((R)-dm-binap)]Cl, E: $Ru(OAc)_2((R)$-dm-segphos), F: [RuCl(p-cymene)((R)-dm-segphos)]Cl.
[b]Determined by GLC analysis after treatment with 7N ammonia/methanol.
[c]Determined by HPLC analysis after conversion to the methyl 3-(4-nitrobenzoylamino)butanoate.

Example 20

Synthesis of methyl (3R)-3-aminobutanoate p-toluenesulfonate

Under a nitrogen atmosphere, a mixture of [$RuCl_2$(p-cymene)]$_2$ (0.527 g, 0.861 mmol), (R)-DM-SEGPHOS (1.276 g, 1.77 mmol), and ammonium acetate (0.664 g, 8.61 mmol) was stirred in 1,4-dioxane (10 mL) at 120° C. for 5 hours and then cooled to room temperature. The resultant mixture was added to a mixture of methyl acetoacetate (100.00 g, 861 mmol), ammonium acetate (66.38 g, 861 mmol) and methanol (500 mL) in a 1 L stainless steel autoclave. The reaction mixture was stirred under a hydrogen pressure of 3 MPa at 85° C. for 8 hours. After completion of the reaction, the solvent was removed by evaporation to give methyl (3R)-3-aminobutanoate acetate as a crude material (161.20 g). The crude product was treated with 7N ammonia/methanol and analyzed by GLC using a capillary column temperature for 1 hour and cooled down to −10° C. to precipitate a solid. The solid was collected by filtration to give methyl (3R)-3-aminobutanoate p-toluenesulfonate (185.12 g, white crystal) in 74.2% yield. The enantiomeric excess of the product obtained above was determined to be 97.9% ee after conversion into methyl (3R)-3-(4-nitrobenzoylamino) butanoate in a similar manner to the crude product.

mp: 112-113° C. $[\alpha]_D^{20}$ −10.1 (c=1.19, MeOH) $^1$H-NMR (CD$_3$OD): δ; 1.32 (d, J=6.8 Hz, 3H), 2.36 (s, 3H), 2.68 (d, J=6.6 Hz, 2H), 3.58-3.70 (m, 1H), 3.71 (s, 3H), 7.23 (d, J=7.8 Hz, 2H), 7.70 (d, J=6.5 Hz, 2H).

Example 21

Synthesis of methyl (3R)-3-aminopentanoate $Ru(OAc)_2((R)$-dm-segphos) (1.21 g, 1.28 mmol), methyl 3-oxopentanoate (50.0 g, 384 mmol), ammonium acetate (29.6 g, 384 mmol) and methanol (500 mL) were placed in a 1 L stainless steel autoclave under nitrogen atmosphere, and then the mixture was stirred under a hydrogen pressure of 3 MPa at 80° C. for 16 hours. After completion of the reaction, the solvent was removed by evaporation. To the residue, toluene (500 mL) was added, and then a 28% solution of sodium methoxide in methanol (66.7 g, 346 mmol) was added at room temperature. After the additions, the mixture was stirred at room temperature for 1 hour, and then the precipitate was filtered off. The filtrate was evaporated and the residue was then distilled to give methyl (3R)-3-aminopentanoate (32.0 g, colorless oil) in 63.5% yield. The enantiomeric excess of the product obtained above was determined to be 98.4% ee by HPLC analysis using a CHIRALCEL OD-H column after conversion into methyl (3R)-3-(4-nitrobenzoylamino)pentanoate.

bp: 40° C./133 Pa $^1$H-NMR (CDCl$_3$): δ; 0.94 (t, J=7.4 Hz, 3H), 1.35-1.49 (m, 2H), 1.50 (brs, 2H), 2.26 (dd, J=9.0, 15.6 Hz, 1H), 2.48 (dd, J=4.0, 15.6 Hz, 1H), 3.08-3.14 (m, 1H), 3.69 (s, 3H).

Example 22

Synthesis of methyl (3S)-3-amino-3-phenylpropionate

Ru(OAc)$_2$((R)-dm-binap) (13.4 mg, 0.0140 mmol), methyl benzoylacetate (500 mg, 2.806 mmol), ammonium acetate (216 mg, 2.806 mmol) and methanol (2.5 mL) were placed in a 100 mL stainless steel autoclave under nitrogen atmosphere, and the mixture was stirred at 80° C. for 1 hour. The reaction mixture was cooled down to room temperature and further stirred under a hydrogen pressure of 3 MPa at 80° C. for 15 hours. After completion of the reaction, the solvent was removed by evaporation and the residue was purified by column chromatography on silica gel (eluent: hexane/ethyl acetate/triethylamine=50/50/5-0/95/5) to give methyl (3S)-3-amino-3-phenylpropionate (201 mg) as a colorless oil in 40.0% yield. The enantiomeric excess of the product was determined to be 96.7% ee by HPLC analysis using a SUMICHIRAL OA-4100R column (available from SUMIKA CHEMICAL ANALYSIS SERVICE LTD.) after conversion into methyl (3S)-3-(4-nitrobenzoylamino)-3-phenylpropionate.

$^1$H-NMR (CDCl$_3$): δ; 1.73 (s, 2H), 2.67 (d, J=6.8 Hz, 2H), 3.68 (s, 3H), 4.42 (t, J=6.8 Hz, 1H), 7.20-7.45 (m, 5H).

Example 23

Synthesis of ethyl (3S)-3-amino-3-phenylpropionate

Ru(OCOCH$_3$)$_2$((R)-dm-binap)(12.4 mg, 0.0130 mmol), ethyl benozylacetate (500 mg, 2.601 mmol), ammonium acetate (201 mg, 2.601 mmol) and ethanol (2.5 mL) were placed in stainless steel autoclave under atmosphere of nitrogen, and the mixture was stirred at 80° C. for 3 hours. The reaction mixture was cooled down to room temperature and further stirred under a hydrogen pressure of 3 MPa at 80° C. for 15 hours. After completion of the reaction, the solvent was removed by evaporation and the residue was purified by column chromatography on silica gel (eluent:hexane ethyl acetate/triethylamine=50/50/5-0/95/5) to give ethyl (3S)-3-amino-3-phenylpropionate (149 mg) as a colorless oil in 29.6% yield. The resulting ethyl (3S)-3-amino-3-phenylpropionate was acetylated with acetic anhydride in the presence of triethylamine to convert into ethyl (3S)-3-acetamido-3-phenylpropionate, and the enantiomeric excess of the product was found to be 93.6% ee by GLC analysis using a capillary column CP-Cirasil DEX-CB.

$^1$H-NMR(CDCl$_3$):δ; 1.23 (t, J=7.2 Hz, 3H), 2.04 (brs, 2H), 2.66 (d, J=6.8 Hz, 2H), 4.14 (q, J=7.2 Hz, 2H), 4.42 (t, J=6.8 Hz, 1H), 7.23-7.28 (m, 1H), 7.31-7.39 (m, 4H) $^{13}$C-NMR (CDCl$_3$):δ; 14.1, 44.2, 52.6, 60.5, 126.2, 127.4, 128.6, 144.6, 172.0 EI-MS(m/z):194 ([M]$^+$)

Example 24

Synthesis of methyl (3R)-3-(4-trifluoromethylphenylamino)pentanoate

[RuCl(p-cymene)((R)-segphos)]Cl(17.6 mg, 0.0192 mmol), methyl 3-oxopentanoate (500 mg, 3.842 mmol), 4-trifluoromethylaniline (619 mg, 3.842 mmol) and 2-propanol (2.5 mL) were placed in a 2.5 mL-stainless autoclave under atmosphere of nitrogen, and the mixture was stirred under a hydrogen pressure of 3 MPa at 80° C. for 15 hours. After completion of the reaction, the solvent was removed by evaporation in vacuo, and the residue was purified by column chromatography on silica gel (eluent: hexane ethyl acetate=3/1) to give methyl (3R)-3-(4-trifluoromethylphenylamino)-pentanoate (109 mg) as a colorless oil in 10.3% yield. The enantiomeric excess of the product was found to be 92.7% ee determined by HPLC analysis using a SUMICHIRAL OA-2500 column (available from SUMIKA CHEMICAL ANALYSIS SERVICE LTD.).

$^1$ H-NMR(CDCl$_3$):δ;0.97 (t, J=7.4 Hz, 3H), 1.58-1.68 (m, 2H), 2.55 (d, J=6.1 Hz, 2H), 3.66 (s, 3H), 3.77-3.81 (m, 1H), 4.13 (brs, 1H), 6.62 (d, J=8.5 Hz, 2H), 7.39 (d, J=11.4 Hz, 2H).

Example 25

Synthesis of methyl (+)-3-amino-3-thiophen-2-yl-propionate

Ru(OCOCH$_3$)$_2$((S)-segphos)(45.0 mg, 0.543 mmol), methyl 2-(2-thenoyl)acetate (1.00 g, 5.428 mmol), ammonium acetate (0.418 g, 5.428 mmol) and methanol (5 mL) were placed in a 2.5 mL-stainless autoclave under atmosphere of nitrogen, and the mixture was stirred at 80° C. for 3 hours. The reaction mixture was cooled down to room temperature and further stirred under a hydrogen pressure of 3 MPa at 80° C. for 15 hours. After completion of the reaction, the solvent was removed by evaporation in vacuo and the residue was purified by silica gel chromatography (eluent hexane ethyl acetate/triethylamine=50/50/5) to give methyl (+)-3-amino-3-thiophen-2-yl-propionate (270 mg) as a colorless oil in 26.8% yield. The resulting methyl (+)-3-amino-3-thiophen-2-yl-propionate was converted into methyl 3-(4-nitrobenzoylamino)-3-thiophen-2-yl-propionate, and the enantiomeric excess of the product was found to be 95.7% ee by HPLC analysis using a SUMICHIRAL OA-4100 column (available from SUMIKA CHEMICAL ANALYSIS SERVICE LTD.).

$[α]_D^{23}$ 10.6° (c=1.04, CHCl$_3$) $^1$H-NMR(CDCl$_3$):δ; 1.85 (s, 2H), 2.72 (dd, J=16.0, 9.1 Hz, 1H), 2.81 (dd, J=16.0, 4.4 Hz, 1H), 3.70 (s, 3H), 4.70 (dd, J=9.1, 4.4 Hz, 1H), 6.94-6.96 (m, 2H), 7.19-7.21 (m, 1H) $^{13}$C-NMR(CDCl$_3$):δ; 44.3, 48.4, 51.6, 122.8, 123.9, 126.5, 149.1, 171.8 EI-MS(m/z):185 ([M]$^+$)

Example 26

Synthesis of methyl (−)-3-amino-5-methylhexanoate acetate

Ru(OAc)$_2$((R)-dm-binap) (0.201 g, 0.211 mmol), methyl 5-methyl-3-oxohexanoate (10.00 g, 63.2 mmol), ammonium acetate (5.02 g, 63.2 mmol) and methanol (50 mL) were placed in a 100 mL stainless steel autoclave under nitrogen atmosphere, and then the mixture was stirred under a hydrogen pressure of 3 MPa at 80° C. for 24 hours. After completion of the reaction, the solvent was removed by evaporation to give methyl (−)-3-amino-5-methylhexanoate acetate as a crude material (12.70 g). The crude product was treated with 7N ammonia/methanol and analyzed by GLC using a capillary column TC-5HT, indicating that the yield of methyl 3-amino-5-methylhexanoate was 74.4%. The enantiomeric excess of methyl (−)-3-amino-5-methylhexanoate in the crude product was determined to be 97.7% ee by HPLC analysis using a SUMICHIRAL OA-4100R column after conversion into methyl 3-(4-nitrobenzoylamino)-5-methylhexanoate.

The resulting crude material (12.70 g) was recrystallized from methyl acetate to give methyl (−)-3-amino-5-methylhexanoate acetate (5.04 g, white crystal) in 36.7% yield. The enantiomeric excess of the product obtained above was determined to be 99.8% ee after conversion into methyl 3-(4-nitrobenzoylamino)-5-methylhexanoate in a similar manner to the crude product.

mp: 67-70° C. $[\alpha]_D^{20}$−18.0 (c=1.03, MeOH) $^1$H-NMR (CD$_3$OD): δ; 0.94 (d, J=6.4 Hz, 3H), 0.96 (d, J=6.4 Hz, 3H), 1.46-1.56 (m, 2H), 1.62-1.79 (m, 1H), 1.89 (s, 3H), 2.60 (dd, J=7.4, 17.0 Hz, 1H), 2.74 (dd, J=5.1, 17.0 Hz, 1H), 3.49-3.63 (m, 1H), 3.72 (s, 3H).

Example 27

Synthesis of ethyl (3R)-3-amino-5-methylhexanoate

Ru(OCOCH$_3$)$_2$((R)-dm-binap)(5.5 mg, 0.058 mmol), ethyl 5-methyl-3-oxo-hexanoate (500 mg, 2.903 mmol), ammonium acetate (224 mg, 2.903 mmol) and ethanol (2.5 mL) were placed in a 2.5 mL-stainless autoclave under atmosphere of nitrogen, and the mixture was further stirred under a hydrogen pressure of 3 MPa at 80° C. for 15 hours. After completion of the reaction, the solvent was removed by evaporation in vacuo and the residue was purified by column chromatography on silica gel (eluent:hexane ethyl acetate/triethylamine=50/50/5) to give ethyl (−)-3-amino-5-methylhexanoate (175 mg) as a colorless oil in 35.0% yield. The resulting ethyl (−)-3-amino-5-methylhexanoate was converted into ethyl 3-(4-nitrobenzoylamino)-5-methylhexanoate, and the enantiomeric excess of the product was found to be 97.3% ee by HPLC analysis using a CHIRALCEL OD-H column.

$[\alpha]_D^{23}$−14.0° (c=1.02, CH$_3$CH$_2$OH) $^1$H-NMR(CDCl$_3$):δ; 0.89 (d, J=6.5 Hz, 3H), 0.90 (d, J=6.5 Hz, 3H), 1.25 (t, J=7.2 Hz, 3H), 1.10-1.38 (m, 2H), 1.58 (brs, 2H), 1.55-1.80 (m, 1H), 2.21 (dd, J=8.8, 15.7 Hz, 1H), 2.42 (dd, J=4.0, 15.7 Hz, 1H), 3.15-3.31 (m, 1H), 4.14 (q, J=7.2 Hz, 2H)

Example 28

Synthesis of methyl (−)-3-amino-4-methylpentanoate acetate

Ru(OAc)$_2$((R)-dm-binap) (0.221 g, 0.231 mmol), methyl 3-oxo-4-methylpentanoate (10.00 g, 69.4 mmol), ammonium acetate (5.52 g, 69.4 mmol) and methanol (50 mL) were placed in a 100 mL stainless steel autoclave under nitrogen atmosphere, and then the mixture was stirred under a hydrogen pressure of 3 MPa at 80° C. for 67 hours. After completion of the reaction, the solvent was removed by evaporation to give methyl (−)-3-amino-4-methylpentanoate acetate as a crude material (11.42 g). The crude product was treated with 7N ammonia/methanol and analyzed by GLC using a capillary column TC-5HT, indicating that the yield of methyl (−)-3-amino-4-methylpentanoate was 85.7%. The enantiomeric excess of methyl (−)-3-amino-4-methylpentanoate in the crude product was determined to be 97.8% ee by HPLC analysis using a SUMICHIRAL OA-4100R column after conversion into methyl 3-(4-nitrobenzoylamino)-4-methylpentanoate.

The resulting crude material (11.42 g) was recrystallized from methyl acetate to give methyl (−)-3-amino-4-methylpentanoate acetate (2.55 g, white crystal) in 17.1% yield. The enantiomeric excess of the product obtained above was determined to be 99.8% ee after conversion into methyl 3-(4-nitrobenzoylamino)-4-methylpentanoate in a similar manner to the crude product.

mp: 65-67° C. $[\alpha]_D^{20}$−28.5 (c=1.01, MeOH) $^1$H-NMR (CD$_3$OD): δ; 0.99 (d, J=6.8 Hz, 3H), 1.01 (d, J=6.8 Hz, 3H), 1.90 (s, 3H), 1.86-2.02 (m, 1H), 2.56 (dd, J=8.4, 17.2 Hz, 1H), 2.75 (dd, J=4.2, 17.2 Hz, 1H), 3.30-3.40 (m, 1H), 3.73 (s, 3H).

Example 29

Synthesis of methyl (3R)-3-amino-4-phenylbutanoate p-toluenesulfonate

Ru(OAc)$_2$((R)-dm-binap) (0.248 g, 0.260 mmol), methyl 3-oxo-4-phenylbutanoate (10.00 g, 52.0 mmol), ammonium acetate (4.01 g, 52.0 mmol) and methanol (50 mL) were placed in a 200 mL stainless steel autoclave under nitrogen atmosphere, and the mixture was stirred at 80° C. for 2 hours. The reaction mixture was cooled down to room temperature and further stirred under a hydrogen pressure of 3 MPa at 80° C. for 14 hours. After completion of the reaction, the solvent was removed by evaporation to give methyl (3R)-3-amino-4-phenylbutanoate as a crude material (13.01 g). The enantiomeric excess of methyl (3R)-3-amino-4-phenylbutanoate in the crude product was determined to be 94.7% ee by HPLC analysis using a SUMICHIRAL OA-4100R column after conversion into methyl (3R)-3-(4-nitrobenzoylamino)-4-phenylbutanoate.

The resulting crude material (13.01 g) was dissolved in methanol (15 mL), and to the solution was added dropwise a solution of p-toluenesulfonic acid monohydrate (9.90 g, 52.0 mmol) in methanol (25 mL) at 50° C. over a period of 30 minutes. The mixture was stirred at room temperature for 1 hour and cooled down to 0° C. to precipitate a solid. The solid was collected by filtration to give methyl (3R)-3-amino-4-phenylbutanoate p-toluenesulfonate (8.34 g, white crystal) in 41.8% yield. The enantiomeric excess of the product obtained above was determined to be 99.8% ee after conversion into methyl (3R)-3-(4-nitrobenzoylamino)-4-phenylbutanoate in a similar manner to the crude product.

mp: 172-173° C. $[\alpha]_D^{20}$−6.9 (c=1.24, MeOH) $^1$H-NMR (CD$_3$OD): δ; 2.36 (s, 3H), 2.58 (dd, J=7.2, 17.3 Hz, 1H), 2.69 (dd, J=5.2, 17.3 Hz, 1H), 2.89 (dd, J=8.4, 14.0 Hz, 1H), 3.03 (dd, J=6.4 Hz, 1H), 3.68 (s, 3H), 3.74-3.88 (m, 1H), 7.20-7.40 (m, 7H), 7.70 (d, J=8.4 Hz, 2H).

Furthermore, the resultant mother liquid was evaporated and the residue was then recrystallized from methanol-methyl acetate to give methyl (3R)-3-amino-4-phenylbutanoate p-toluenesulfonate (6.10 g, white crystal) in 30.6% yield. The enantiomeric excess of the product was determined to be 94.7% ee after conversion into methyl (3R)-3-(4-nitrobenzoylamino)-4-phenylbutanoate in a similar manner to the crude product.

Comparison of the sign of the specific rotation of the product with the literature data ($[\alpha]_D^{27}$+7.0 (c=1.05, MeOH), (S)-enantiomer, EP0136883) established its absolute configuration as 3R.

Example 30

Synthesis of methyl (–)-3-(benzylamino)butanoate

Ru(OCOCH$_3$)$_2$((R)-dm-binap)(20.5 mg, 0.0215 mmol), methyl acetoacetate (500 mg, 4.305 mmol), benzylamine (461 mg, 4.305 mmol) and methanol (2.5 mL) were placed in a 2.5 mL-stainless autoclave under atmosphere of nitrogen, and the mixture was stirred at 80° C. for 3 hours. The reaction mixture was cooled down to room temperature, and acetic acid (259 mg, 4.305 mmol) was added thereto. The mixture was further stirred under a hydrogen pressure of 3 MPa at 80° C. for 15 hours. After completion of the reaction, the solvent was removed by evaporation in vacuo, and the residue was purified by column chromatography on silica gel (eluent: hexane ethyl acetate/triethylamine=75/25/5) to give the objective methyl (–)-3-(benzylamino)butanoate (141 mg) as a colorless oil in 15.8% yield. The enantiomeric excess of the resulting methyl (–)-3-(benzylamino)butanoate was determined to be 44.5% ee by HPLC analysis using a CHIRALCEL OD-H column.

$[\alpha]_D^{23}$–4.0° (c=0.97, CHCl$_3$) $^1$H-NMR(CDCl$_3$):δ; 1.16 (d, J=6.4 Hz, 3H), 1.72 (brs, 1H), 2.38 (dd, J=6.1, 15.3 Hz, 1H), 2.51 (dd, J=6.8, 15.3 Hz, 1H), 3.08-3.21 (m, 1H), 3.67 (s, 3H), 3.75 (d, J=12.8 Hz, 1H), 3.84 (d, J=12.8 Hz, 1H), 7.19-7.45 (m, 5H)

Example 31

Synthesis of methyl (–)-3-(benzylamino)butanoate

Working up procedure and after treatment in the same manner as in Example 19 by use of Ru(OCOCH$_3$)$_2$((R)-tolbinap)(38.7 mg, 0.0431 mmol), methyl acetoacetate (1.00 g, 8.612 mmol), benzylamine (0.923 g, 8.612 mmol), methanol (5 mL) and acetic acid (0.517 g, 8.612 mmol) in place of Ru(OCOCH$_3$)$_2$((R)-dm-binap)(20.5 mg, 0.0215 mmol), methyl acetoacetate (500 mg, 4.305 mmol), benzylamine (461 mg, 4.305 mmol), methanol (2.5 mL) and acetic acid (259 mg, 4.305 mmol) gave methyl (–)-3-(benzylamino)butanoate (176 mg) as a colorless oil in 9.9% yield. The enantiomeric excess of the product was determined to be 24.0% ee in the same way as in Example 29.

$[\alpha]_D^{23}$–2.1° (c=1.05, CHCl$_3$)

Example 32

Synthesis of tert-butyl (2S,3S)-3-amino-2-hydroxy-4-phenylbutanoate acetate

Ru(OAc)$_2$((S)-dm-segphos) (0.138 g, 0.147 mmol), tert-butyl 2-benzyloxy-3-oxo-4-phenylbutanoate (5.00 g, 14.7 mmol), ammonium acetate (1.13 g, 14.7 mmol), methanol (25 mL) and tetrahydrofuran (25 mL) were placed in a 200 mL stainless steel autoclave, and the mixture was stirred at 90° C. under a hydrogen pressure of 3 MPa for 13 hours. After completion of the reaction, the solvent was removed by evaporation to give tert-butyl 3-amino-2-benzyloxy-4-phenylbutanoate acetate as a crude material (6.10 g). The ratio of anti and syn diastereoisomer (86:14) was determined by HPLC analysis using a CHIRALPAK AD-RH column (available from DAICEL CHEMICAL INDUSTRIES, LTD). The enantiomeric excess of the crude product was determined to be 98.6% ee (anti diastereoisomer) and 95.1% ee (syn diastereoisomer) by HPLC analysis using a CHIRALCEL OD-H column after conversion into tert-butyl 3-(4-nitrobenzoylamino)-2-benzyloxy-4-phenylbutanoate.

The resulting crude material (6.10 g) and Pd-C (0.90 g) were dissolved in acetic acid (90 mL). The mixture was then stirred at 60° C. under a under a hydrogen pressure of 2 MPa for 18 hours. After removal of the catalyst by filtration, the resultant mother liquid was evaporated. The residue was then recrystallized from ethyl acetate to give tert-butyl (2S,3S)-3-amino-2-hydroxy-4-phenylbutanoate acetate (1.36 g, white crystal) as a single diastereoisomer in 29.8% yield.

mp: 108-110° C. $[\alpha]_D^{20}$–0.5 (c=1.05, MeOH) $^1$H-NMR (CDCl$_3$): δ; 1.51 (s, 9H), 2.01 (s, 3H), 2.62-2.83 (m, 2H), 3.46-3.58 (m, 1H), 4.33 (d, J=3.0 Hz, 1H), 7.18-7.37 (m, 5H).

Comparison of the $^1$H NMR spectroscopic data for the free β-amino ester of the product obtained above, tert-butyl 3-amino-2-hydroxy-4-phenylbutanoate, with the literature data (Tetrahedron 1994, vol. 50, No. 13, p. 3975 to 3986) established its anti relative stereochemistry, while the sign of its specific rotation established its absolute configuration as (2S,3S).

INDUSTRIAL APPLICABILITY

The process according to the present invention can synthesize effectively and industrially amino acid derivatives, particularly optically active amino acid derivatives, useful as intermediates for medicines, agrochemicals, etc.

The invention claimed is:
1. A process for producing an optically active β-amino acid derivative of the formula (2-2):

wherein
R$^1$ is an optionally substituted hydrocarbon group or an optionally substituted heterocyclic group;
R$^3$ is an optionally substituted alkoxy group, an optionally substituted aryloxy group, an optionally substituted aralkyloxy group, hydroxy, —NR$^a$R$^b$ (R$^a$ and R$^b$ are each independently a hydrogen atom, an optionally substituted hydrocarbon group, an optionally substituted acyl group, —SO$_2$A$^1$ (A$^1$ is an optionally substituted hydrocarbon group or a substituted amino group), —COOR$^c$ (R$^c$ is an optionally substituted hydrocarbon group)), or an optionally substituted heterocyclic group;
R$^{11}$ is a hydrogen atom, an optionally substituted hydrocarbon group, an optionally substituted alkoxy group, an optionally substituted aryloxy group, an optionally substituted aralkyloxy group or hydroxyl, wherein when R$^{11}$ is an optionally substituted hydrocarbon group, an optionally substituted alkoxy group, an optionally substituted aryloxy group, an optionally substituted aralkyloxy group or hydroxyl, the carbon atom to which $R^{11}$ is attached is chiral;

$R^1$ and $R^{11}$, $R^{11}$ and $R^3$, or $R^3$ and $R^1$, taken together, may form a ring;

X' is an acid;

b is 1; and

* is a chiral carbon atom, which comprises reacting a β-keto acid derivative of the formula (1-1):

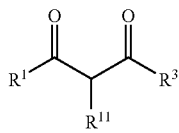

(1-1)

wherein $R^1$, $R^{11}$ and $R^3$ have each the same meaning as defined above, with an ammonium salt in the presence of a chiral catalyst and hydrogen;

the ammonium salt is represented by the formula (3):

$NH_3 \cdot aX'$ (3)

wherein X' has the same meaning as defined above; and a is 1.

2. The process according to claim 1, wherein the chiral catalyst is a transition metal complex.

3. The process according to claim 2, wherein the transition metal complex is a complex of metal of Group VIII (Groups 8 to 10).

4. The process according to claim 2, wherein the transition metal complex has a chiral ligand.

5. The process according to claim 4, wherein the chiral ligand is a chiral phosphine ligand.

6. The process according to claim 1, wherein the chiral catalyst is a chiral transition metal complex of the formula (7) or (8):

$M_m L_n X_p Y_q$ (7)

$[M_m L_n X_p Y_q]Z_s$ (8)

wherein M is a transition metal of Group VIII (Groups 8 to 10); L is a chiral ligand; X is a halogen atom, a carboxylato group, allyl, 1,5-cyclooctadiene or norbornadiene; Y is a ligand; Z is an anion or a cation; m, n, p, q and s are each an integer of 0 to 5.

7. The process according to claim 1, wherein the chiral catalyst is a mixture of a chiral ligand and a transition metal compound.

8. The process according to claim 1, wherein reacting the β-keto acid derivative of the formula (1-1) with the ammonium salt is conducted in the presence of an inorganic acid, an organic acid, or a fluorine-containing alcohol.

* * * * *